United States Patent
Aguirre et al.

(10) Patent No.: US 8,545,519 B2
(45) Date of Patent: Oct. 1, 2013

(54) MEDICAL DEVICES WITH DETACHABLE PIVOTABLE JAWS

(75) Inventors: Andres F. Aguirre, Chicago, IL (US); Vihar C. Surti, Winston-Salem, NC (US); Michelle D. Martinez, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 92 days.

(21) Appl. No.: 13/186,427

(22) Filed: Jul. 19, 2011

(65) Prior Publication Data

US 2012/0016391 A1    Jan. 19, 2012

Related U.S. Application Data

(63) Continuation-in-part of application No. 12/971,873, filed on Dec. 17, 2010.

(60) Provisional application No. 61/289,297, filed on Dec. 22, 2009, provisional application No. 61/391,881, filed on Oct. 11, 2010.

(51) Int. Cl.
*A61B 17/10* (2006.01)
*A61B 17/08* (2006.01)

(52) U.S. Cl.
USPC ............... 606/142; 606/151; 606/157

(58) Field of Classification Search
USPC ............ 606/139, 142, 143, 205, 208, 157, 606/158, 219, 151
See application file for complete search history.

(56) References Cited

U.S. PATENT DOCUMENTS

| | | |
|---|---|---|
| 720,385 A | 2/1903 | Storle |
| 3,958,576 A | 5/1976 | Komiya |
| 4,467,802 A | 8/1984 | Maslanka |
| 4,512,345 A | 4/1985 | Green |
| 4,569,131 A | 2/1986 | Falk et al. |
| 4,733,664 A | 3/1988 | Kirsch et al. |
| 4,763,668 A | 8/1988 | Macek et al. |
| 4,765,335 A | 8/1988 | Schmidt et al. |
| 4,805,618 A | 2/1989 | Ueda et al. |
| 4,950,273 A | 8/1990 | Briggs |
| 5,100,418 A | 3/1992 | Yoon et al. |

(Continued)

FOREIGN PATENT DOCUMENTS

| | | |
|---|---|---|
| DE | 19534320 | 2/1997 |
| DE | 19750878 A1 | 5/1999 |

(Continued)

OTHER PUBLICATIONS

International Search Report/Written Opinion for PCT/US2009/069270 (May 17, 2010).

(Continued)

*Primary Examiner* — Julian W Woo
(74) *Attorney, Agent, or Firm* — Brinks Hofer Gilson & Lione

(57) ABSTRACT

Medical systems, devices and methods are provided for engaging tissue, e.g. for clipping tissue, closing a perforation or performing hemostasis. Generally, the medical system including a housing, first and second jaws rotatable relative to the housing, a driver, and an elongate drive wire. The elongate drive wire may be disconnected from the driver, first and second jaws, and the housing, which are left in vivo engaged with the tissue.

22 Claims, 21 Drawing Sheets

(56) References Cited

U.S. PATENT DOCUMENTS

| | | |
|---|---|---|
| 5,141,519 A | 8/1992 | Smith et al. |
| 5,152,778 A | 10/1992 | Bales, Jr. et al. |
| 5,174,276 A | 12/1992 | Crockard |
| 5,192,298 A | 3/1993 | Smith et al. |
| 5,201,743 A | 4/1993 | Haber et al. |
| 5,209,747 A | 5/1993 | Knoepfler |
| 5,275,608 A | 1/1994 | Forman et al. |
| 5,275,613 A | 1/1994 | Haber et al. |
| 5,275,615 A | 1/1994 | Rose |
| 5,282,806 A | 2/1994 | Haber et al. |
| 5,318,589 A | 6/1994 | Lichtman |
| 5,368,606 A | 11/1994 | Marlow et al. |
| 5,471,992 A | 12/1995 | Banik et al. |
| 5,571,137 A | 11/1996 | Marlow et al. |
| 5,618,303 A | 4/1997 | Marlow et al. |
| 5,702,407 A | 12/1997 | Kaji |
| 5,766,184 A | 6/1998 | Matsuno et al. |
| 5,766,189 A | 6/1998 | Matsuno |
| 5,792,165 A | 8/1998 | Kilieman et al. |
| 5,797,923 A | 8/1998 | Aiyar et al. |
| 5,964,779 A | 10/1999 | Mayenberger et al. |
| 6,059,719 A | 5/2000 | Yamamoto et al. |
| 6,358,197 B1 | 3/2002 | Silverman et al. |
| 6,814,742 B2 | 11/2004 | Kimura et al. |
| 6,923,818 B2 | 8/2005 | Muramatsu et al. |
| 7,011,667 B2 | 3/2006 | Kobayashi et al. |
| 7,041,118 B2 | 5/2006 | Muramatsu et al. |
| 7,081,121 B2 | 7/2006 | Muramatsu et al. |
| 7,223,271 B2 | 5/2007 | Muramatsu et al. |
| 7,223,272 B2 | 5/2007 | Francese et al. |
| 7,326,221 B2 | 2/2008 | Sakamoto |
| 7,452,327 B2 | 11/2008 | Durgin et al. |
| 7,488,334 B2 | 2/2009 | Jugenheimer et al. |
| 7,494,461 B2 | 2/2009 | Wells et al. |
| 7,601,159 B2 | 10/2009 | Ewers et al. |
| 7,722,628 B2 | 5/2010 | Stokes et al. |
| 7,727,247 B2 | 6/2010 | Kimura et al. |
| 7,736,372 B2 | 6/2010 | Reydel et al. |
| 7,736,374 B2 | 6/2010 | Vaughan et al. |
| 7,740,639 B2 | 6/2010 | Hummel et al. |
| 7,744,613 B2 | 6/2010 | Ewers et al. |
| 7,766,810 B2 | 8/2010 | Ohdaira |
| 7,776,057 B2 | 8/2010 | Laufer et al. |
| 7,815,652 B2 | 10/2010 | Messerly et al. |
| 8,083,668 B2 | 12/2011 | Durgin et al. |
| 8,088,061 B2 | 1/2012 | Wells et al. |
| 8,172,859 B2 * | 5/2012 | Matsuno et al. ............... 606/142 |
| 2002/0151916 A1 | 10/2002 | Muramatsu et al. |
| 2002/0173805 A1 | 11/2002 | Matsuno et al. |
| 2002/0177861 A1 | 11/2002 | Sugiyama et al. |
| 2003/0069592 A1 | 4/2003 | Adams et al. |
| 2003/0097146 A1 | 5/2003 | Montalvo et al. |
| 2004/0044363 A1 | 3/2004 | Fowler |
| 2005/0059985 A1 | 3/2005 | Kimura |
| 2005/0101991 A1 | 5/2005 | Ahlberg et al. |
| 2005/0234296 A1 | 10/2005 | Saadat et al. |
| 2005/0251183 A1 | 11/2005 | Buckman et al. |
| 2005/0272977 A1 | 12/2005 | Saadat et al. |
| 2006/0084886 A1 | 4/2006 | Reydel |
| 2006/0155308 A1 | 7/2006 | Griego |
| 2006/0258905 A1 | 11/2006 | Kaji et al. |
| 2006/0259045 A1 | 11/2006 | Damarati |
| 2007/0073185 A1 | 3/2007 | Nakao |
| 2007/0135678 A1 | 6/2007 | Suzuki |
| 2007/0239162 A1 | 10/2007 | Bhatnagar et al. |
| 2007/0250113 A1 | 10/2007 | Hegeman et al. |
| 2007/0287993 A1 | 12/2007 | Hinman et al. |
| 2008/0004656 A1 | 1/2008 | Livneh |
| 2008/0147113 A1 | 6/2008 | Nobis et al. |
| 2008/0171907 A1 | 7/2008 | Long et al. |
| 2008/0228199 A1 | 9/2008 | Cropper et al. |
| 2008/0228202 A1 | 9/2008 | Cropper et al. |
| 2008/0234703 A1 | 9/2008 | Cropper et al. |
| 2008/0234705 A1 | 9/2008 | Cropper et al. |
| 2008/0255427 A1 | 10/2008 | Satake et al. |
| 2008/0262539 A1 | 10/2008 | Ewers et al. |
| 2008/0269557 A1 | 10/2008 | Marescaux et al. |
| 2008/0269566 A1 | 10/2008 | Measamer |
| 2008/0275441 A1 | 11/2008 | Aue |
| 2008/0287963 A1 | 11/2008 | Rogers et al. |
| 2008/0294178 A1 | 11/2008 | Kortenbach et al. |
| 2008/0300461 A1 | 12/2008 | Shaw et al. |
| 2008/0300624 A1 | 12/2008 | Schwemberger et al. |
| 2009/0005638 A1 | 1/2009 | Zwolinski |
| 2009/0018602 A1 | 1/2009 | Mitelberg et al. |
| 2009/0043316 A1 | 2/2009 | Durgin et al. |
| 2009/0062792 A1 | 3/2009 | Vakharia et al. |
| 2009/0138028 A1 | 5/2009 | Wells et al. |
| 2009/0143794 A1 | 6/2009 | Conlon et al. |
| 2009/0163934 A1 | 6/2009 | Raschdorf, Jr. et al. |
| 2009/0192344 A1 | 7/2009 | Bakos et al. |
| 2009/0221915 A1 | 9/2009 | Voegele et al. |
| 2009/0299385 A1 | 12/2009 | Stefanchik et al. |
| 2009/0306683 A1 | 12/2009 | Zwolinski et al. |
| 2009/0306686 A1 | 12/2009 | Ohdaira |
| 2009/0326518 A1 | 12/2009 | Rabin |
| 2009/0326578 A1 | 12/2009 | Ewers et al. |
| 2010/0042115 A1 | 2/2010 | Saadar et al. |
| 2010/0057078 A1 | 3/2010 | Arts et al. |
| 2010/0057085 A1 | 3/2010 | Holcomb et al. |
| 2010/0130817 A1 | 5/2010 | Conlon |
| 2010/0168787 A1 | 7/2010 | Surti |
| 2010/0179540 A1 | 7/2010 | Marczyk et al. |
| 2010/0198149 A1 | 8/2010 | Fox |
| 2010/0198248 A1 | 8/2010 | Vakharia |
| 2010/0211086 A1 | 8/2010 | Ewers et al. |
| 2010/0217151 A1 | 8/2010 | Gostout et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0249700 A1 | 9/2010 | Spivey |
| 2010/0249808 A1 | 9/2010 | Harada et al. |

FOREIGN PATENT DOCUMENTS

| | | |
|---|---|---|
| DE | 19906360 A1 | 8/2000 |
| DE | 102006003548 | 8/2007 |
| JP | 57-156752 | 9/1982 |
| JP | 60-103946 | 6/1985 |
| JP | 63-6016 | 2/1988 |
| JP | 63-267345 | 11/1988 |
| JP | 63-288147 | 11/1988 |
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 9038093 | 2/1997 |
| JP | 9289989 | 11/1997 |
| JP | 2000-33090 | 2/2000 |
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| WO | WO 9614020 | 5/1996 |
| WO | WO 99/20183 | 4/1999 |
| WO | WO 2004/017839 | 4/2004 |
| WO | WO 2012/051188 | 4/2012 |
| WO | WO 2012/051191 | 4/2012 |
| WO | WO 2012/051200 | 4/2012 |

OTHER PUBLICATIONS

International Search Report/Written Opinion for PCT/US2010/061077 (Apr. 1, 2011).

Medicon Instrument Catalog, pp. 440, 441, 443, 451, 585, 686 (1986).

V. Mueller, The Surgical Armamentarium, pp. F176-F177 (1988).

Annex to Form PCT/ISA/206—Communication Relating to the Results of the Partial International Search for PCT/US2011/055800 (Jun. 28, 2012).

International Search Report and Opinion for PCT/US2011/055780 (Jun. 14, 2012).

International Search Report and Opinion for PCT/US2011/055786 (Jun. 19, 2012).

International Search Report and Opinion for PCT/US2011/065200 (Jun. 13, 2012).

* cited by examiner

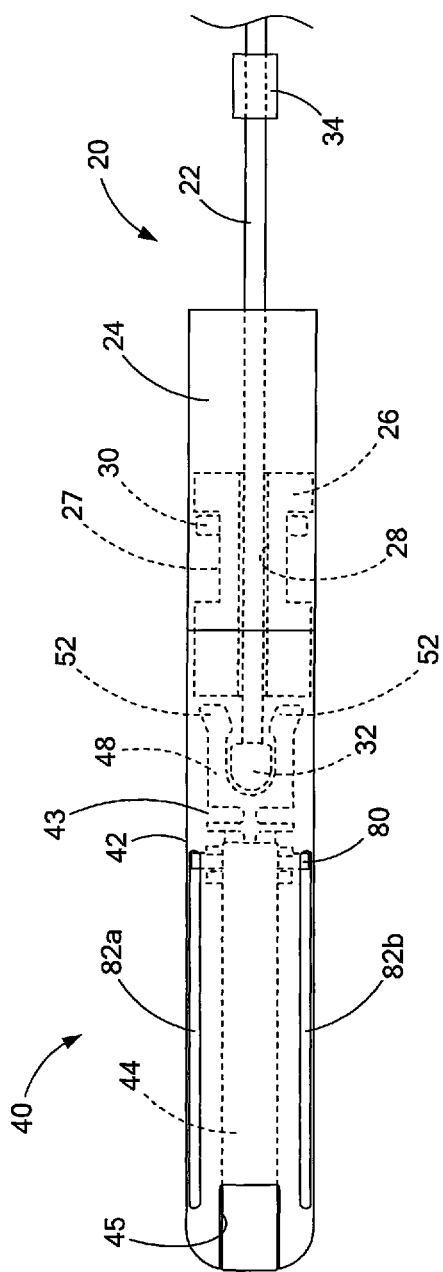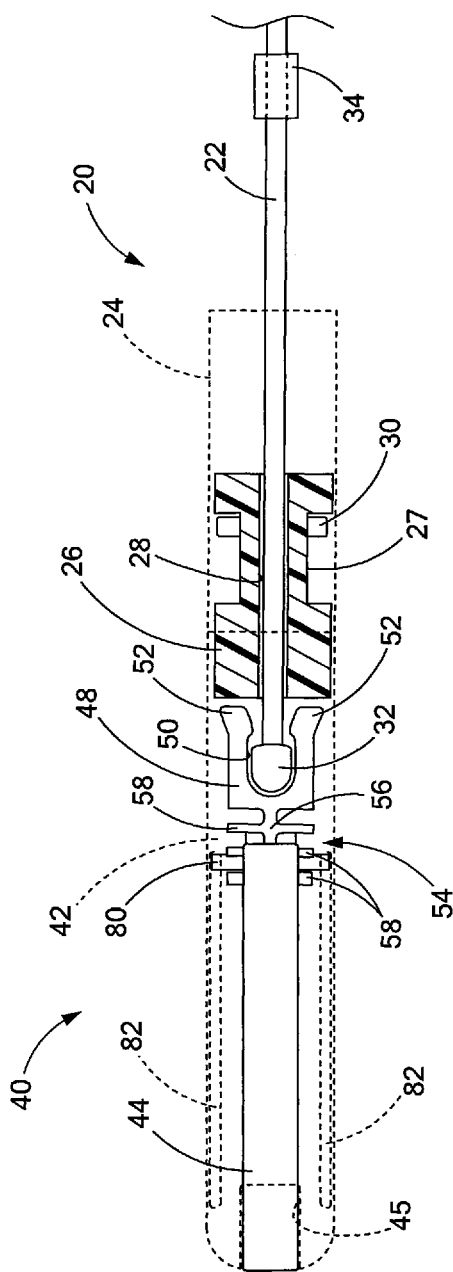
FIG. 1
FIG. 2

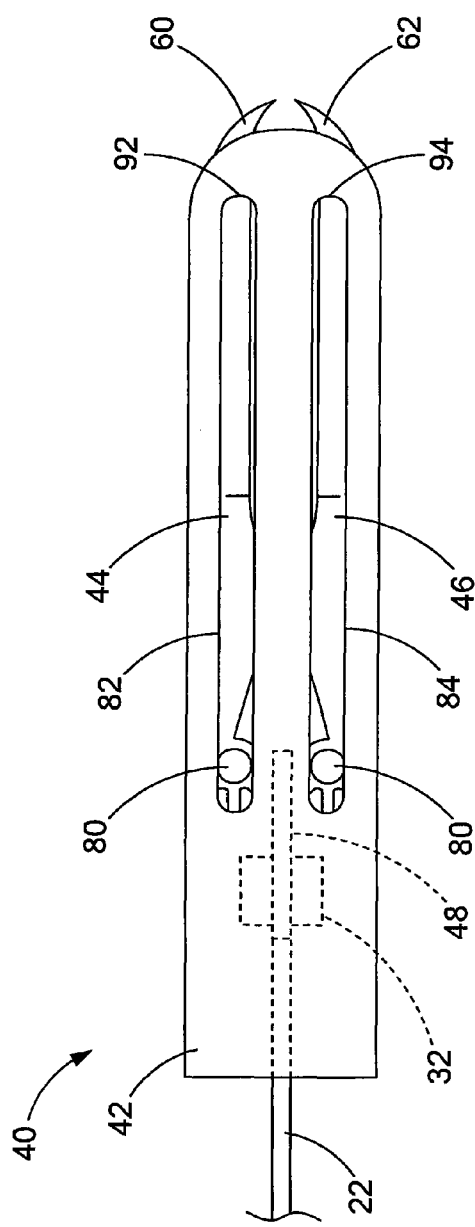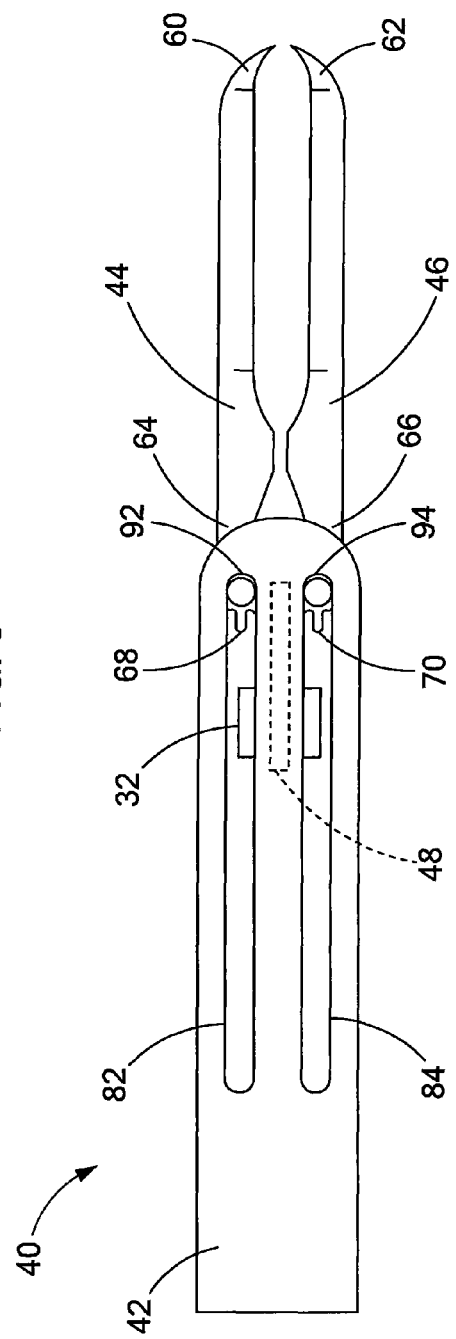
FIG. 8
FIG. 9

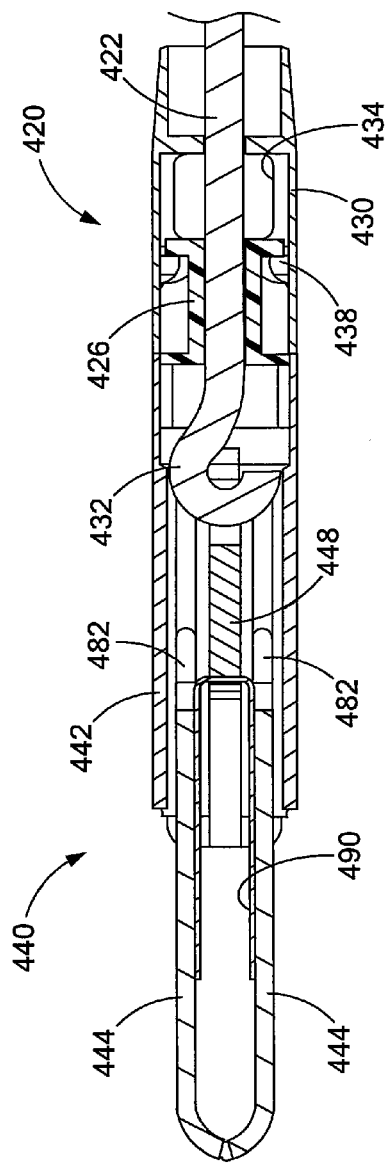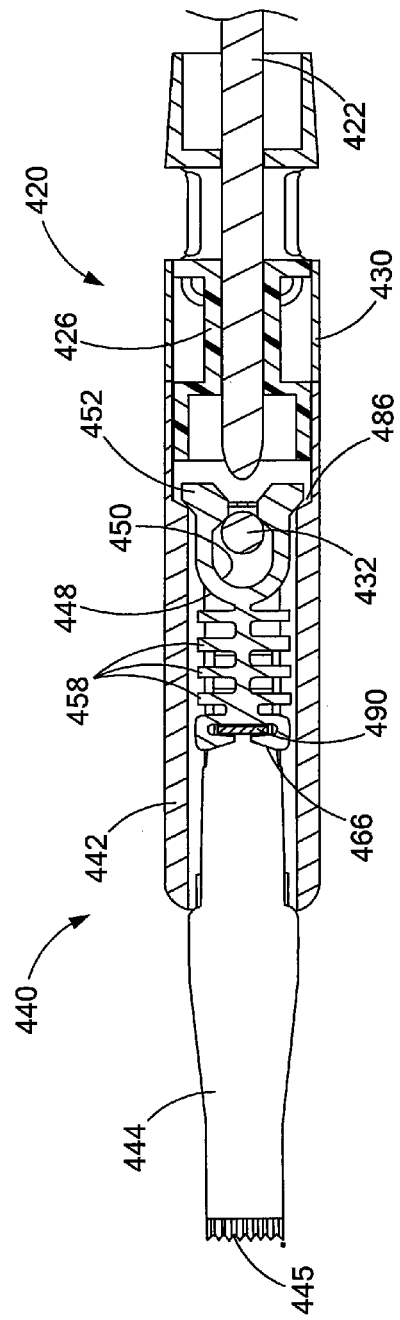
FIG. 31
FIG. 32

MEDICAL DEVICES WITH DETACHABLE PIVOTABLE JAWS

CROSS-REFERENCE TO RELATED APPLICATIONS

This application is a continuation-in-part of U.S. patent application Ser. No. 12/971,873 filed on Dec. 17, 2010, which claims the benefit of U.S. Provisional Application Ser. No. 61/289,297 filed on Dec. 22, 2009, entitled "MEDICAL DEVICES WITH DETACHABLE PIVOTABLE JAWS," and further claims the benefit of the filing date under 35 U.S.C. §119(e) of Provisional U.S. Patent Application Ser. No. 61/391,881 filed Oct. 11, 2010. All of the foregoing applications are hereby incorporated by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

BRIEF SUMMARY

The invention may include any of the following aspects in various combinations and may also include any other aspect described below in the written description or in the attached drawings.

In a first aspect, a medical device is provided for engaging tissue, the medical device including a housing, first and second jaws, an elongated drive wire, and a driver. The housing defines an internal passageway and a longitudinal axis extending between proximal and distal ends of the housing. The housing also defines a driver guide surface along the internal passageway. The first and second jaws are rotatable relative to the housing, and each have proximal and distal ends. The driver has a proximal portion engaged with the drive wire and a distal portion engaged with the proximal ends of the first and second jaws. Longitudinal movement of the driver rotates the first and second jaws relative to the housing. The driver also includes an intermediate portion positioned between the proximal and distal portions. The intermediate portion includes a frame and a locking leg connected to the frame, the frame defining an intermediate space. The frame is deformable such that a predetermined longitudinal force differential between the proximal portion and distal portion of the driver causes the frame to deform and the locking leg to move away from the longitudinal axis into a locking position for engaging the driver guide surface.

According to more detailed aspects, the length of the driver increases upon deformation of the frame. The frame circumscribes the intermediate space, and the intermediate space has a general C-shape prior to deformation of the frame, and a generally rectangular shape after deformation of the frame. The longitudinal distance of the intermediate space increases after deformation, and the locking leg preferably rotates away from the longitudinal axis. The driver may also include a neck interconnecting the proximal portion of the driver and the intermediate portion of the driver. In one variation, the neck is breakable upon a second predetermined longitudinal force differential between the proximal portion and the intermediate portion of the driver. The second predetermined longitudinal force differential is greater than the predetermined longitudinal force differential that deforms the frame. In another variation, the neck is not breakable, but rather the proximal portion and its socket deforms to allow the drive wire and related structures to be released, leaving the clip in vivo and locked to the tissue.

According to still further detailed aspects, the frame preferably includes a proximal member extending laterally, a distal member extending laterally, and a pair of side members connecting the proximal and distal members. The locking leg is connected to the distal member and one of the side members, and the distal member defines a deformable area adjacent the locking leg. In some constructions, the distal member, locking leg, and the one side member together deform under the predetermined longitudinal force differential to move the locking leg away from the longitudinal axis. The locking leg may have a general V-shape and define a portion of the intermediate space. The housing's driver guide surface includes a proximal portion and distal portion and a shoulder at the transition between of the proximal and distal portions. The shoulder faces proximally, and the locking leg is positioned to engage the shoulder to limit longitudinal movement of the driver after the locking leg has been moved laterally outwardly by deformation of the frame of the driver.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a top view of a medical system having a medical device for engaging tissue, constructed in accordance with the teachings of the present invention;

FIG. 2 is a top view similar to FIG. 1, but showing the outer structures in dotted lines and the interior sections in solid lines and partial cross section;

FIGS. 8-12 are side views showing operation of the medical system and device depicted in FIGS. 1-5;

FIGS. 31 and 32 are cross-sectional views of another embodiment of the medical system and device depicted in FIG. 1;

DETAILED DESCRIPTION

Figure 3:
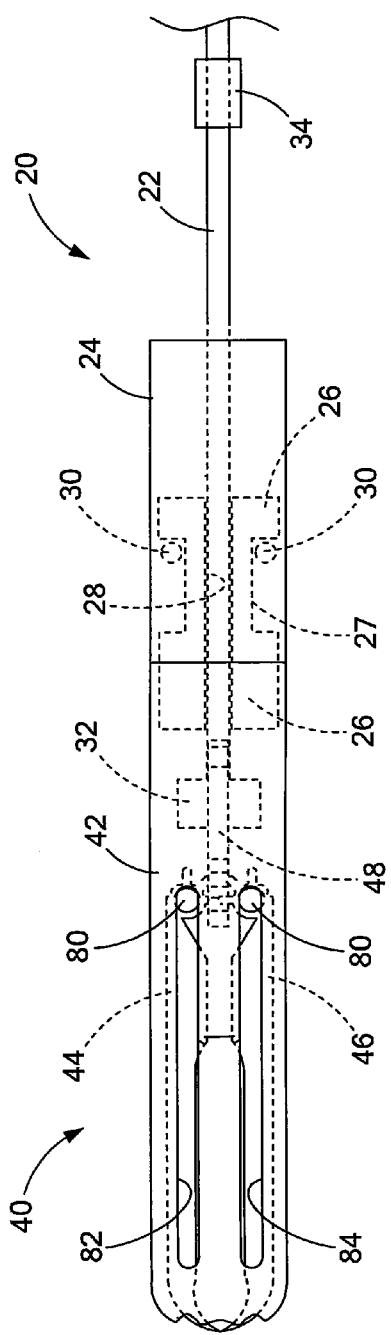
FIG. 3 is a side view of the medical system and device depicted in FIG. 1.
Figure 4:
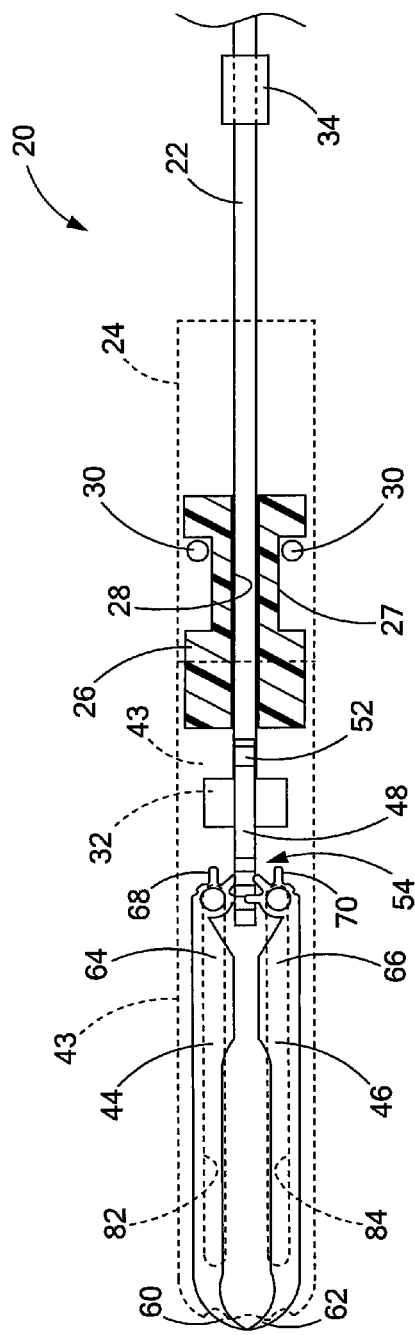
FIG. 4 is a side view similar to FIG. 3, but showing the outer structures in dotted lines and the interior structures in solid lines and partial cross section

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary medical system 20 having a medical device 40 for engaging tissue T (FIG. 11) is shown in FIGS. 1 through 4. The medical system 20 and device 40 are generally sized and structured for operation through the working channel of an endoscope (not shown) or other scope, although the system 20 and device 40 may also be used alone or in conjunction with other elongate devices such as catheters, fiber-optic visualization systems, needles and the like. Generally, the medical system 20 includes a drive wire 22 slidably housed within the distal end 23 of an elongated catheter 24 for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the catheter 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires, metal rods and the like. The drive wire 22 should also be capable of properly transmitting a rotational/torsional force from the proximal end to the distal end to rotate the medical device 40 and jaws 44, 46, and thus it is currently preferred that the drive wire 22 is formed from nitinol (e.g. a nitinol wire) or other superelastic alloy. A connection block 26 is slidably fitted within the distal end 23 of the catheter 24 and defines a bore 28 therethrough which slidably receives the drive wire 22. The exterior of the connection block 26 includes a recessed portion 27, and two pins 30 (e.g., formed from stainless steel wire) are connected to the catheter 24 and positioned within the recessed portion 27 to limit the longitudinal movement of the connection block 26.

A distal end of the drive wire 22 defines a distal head 32 that is sized larger than the drive wire 22, and likewise larger than the bore 28 in the connection block 26. As will be described later herein, the distal head 32 is used to slide the connection block 26 within the catheter 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

Figure 5:
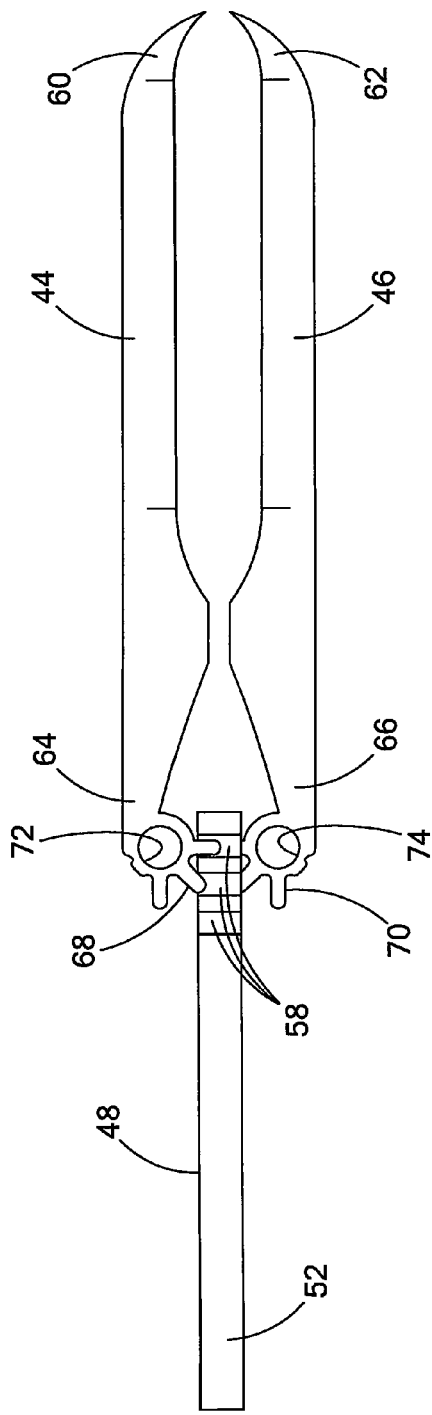
FIG. 5 is a side view of a medical device that is part of the medical system depicted in FIGS. 1-4.

The internal passageway 43 of the housing 42 also receives the first and second jaws 44, 46 and a driver 48 which is used to interconnect the drive wire 22 to the jaws 44, 46. As best seen in FIGS. 1, 2 and 5, the driver 48 has a proximal portion which defines a socket 50 sized to receive enlarged distal head 32 of the drive wire 22. At the proximal entrance of the socket 50, two deflectable locking tabs 52 are formed which rotate relative to the remainder of the driver 48 to increase or decrease the size of the socket 50. The locking tabs 52 may be separately formed and pivotally attached to the driver 48, or may be integrally formed with the driver 48 and formed of a resilient material which flexes to permit rotation of the locking tabs 52 radially inwardly and radially outwardly. A distal portion of the driver 48 defines a rack 54 for engaging and operating the jaws 44, 46. In the depicted embodiment, the rack 54 includes a central spine 56 having teeth 58 projecting away from the central spine 56 and on opposite sides of the spine 56. One set of teeth 58 on one side of the spine 56 generally operate the first jaw 44 while the other set of teeth 58 on the other side of the spine 56 operate the second jaw 46. It will be recognized that the rack 54 may include a single set of teeth or other geared structures that interface with the jaws 44, 46.

As best seen in FIG. 5, the first and second jaws 44, 46 include distal ends 60, 62 that are structured to grasp and engage tissue, generally they have a talon shape as disclosed in 61/141,934 filed Dec. 31, 2008, the disclosure of which is incorporated herein by reference in its entirety. The proximal ends 64, 66 of the first and second jaws 44, 46 each include a pinion gear 68, 70 having a series of teeth. The teeth of the pinion 68, 70 mesh with the teeth of the rack 54 of the driver 48 such that longitudinal translation of the driver 48 induces rotation in the first and second jaws 44, 46 relative to one another. Generally, distal translation of the driver 48 causes the first and second jaws 44, 46 to rotate outwardly away from each other, while proximal retraction of the driver 48 causes the first and second jaws 44, 46 to rotate inwardly toward one another. Pins 80 are fitted through each the proximal ends of the jaws 44, 46, to pivotally connect the jaws to the housing 42. Other structures for forming a pivotal connection may be used, and preferably the pivotal connection is centrally arranged relative to the pinions 68, 70.

Figure 7:
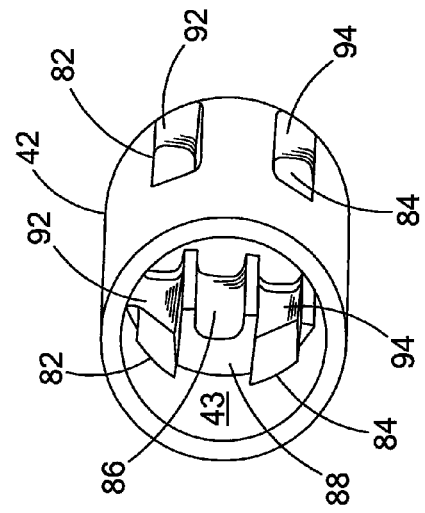
FIG. 7 is a perspective view of the housing depicted in FIG. 6.
Figure 6:
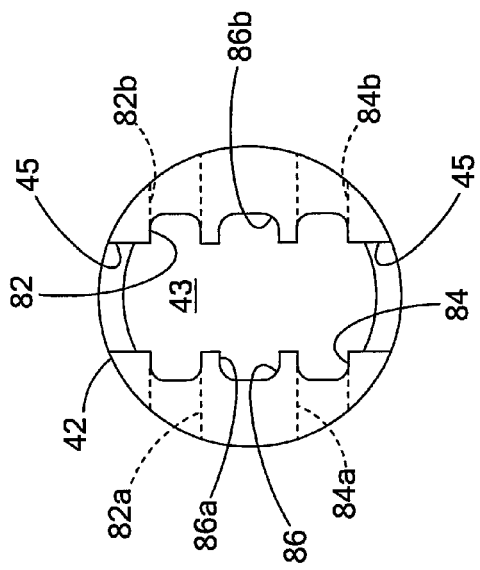
FIG. 6 is a front view of a housing forming a portion of the medical system and device depicted in FIGS. 1-5.

In addition to the jaws 44, 46 being pivotally attached to the housing 42, the first and second jaws 44, 46 are also slidably attached to the housing 42. As best seen in FIGS. 6 and 7 (and in conjunction with FIGS. 1-4) the housing 42 defines a first guide surface 82 for the first jaw 44, and a second guide surface 84 for the second jaw 46. As seen in FIG. 3, the first and second guide surfaces 82, 84 are formed by elongated slots 82a, 82b, 84a, 84b formed in opposing sides of the housing 42 which leaves a thickness of the housing 42 exposed to serve as the guide surface. The slots 82a, 82b are aligned to receive the connecting pin 80 of the first jaw 44, and likewise the slots 84a, 84b are aligned to receive the connecting pin 80 of the second jaw 46. The ends of the slots, for example distal ends 92, 94 shown in FIG. 7, serve to restrict the longitudinal movement of the jaws 44, 46 relative to the housing 42. The proximal ends 64, 66 of the jaws 44, 46 include apertures 72, 74 which receive the pins 80 (FIGS. 1, 2 and 3) that are used to slidably and pivotally connect the first and second jaws 44, 46 to the housing 42.

It can also be seen in FIGS. 6 and 7 that the housing 42 defines a third guide surface 86 which guides the longitudinal movement of the driver 48 within the housing 42. The guide surface 86 in the depicted embodiment includes a left guide surface 86a and a right guide surface 86b formed as C-shaped channels. As shown in FIG. 7, the third guide surface 86 transitions from a smaller proximal width to a larger distal width to define a shoulder 88 at the transition, which will be further described hereinbelow with reference to FIGS. 13 and 14.

As also shown in FIG. 6, the internal passageway 43 of the housing 42 extends through the distal end of the housing, and through which the first and second jaws 44, 46 can extend. Additionally, as shown in FIGS. 1 and 2, the housing 42 defines opposing slots 45 which are sized to permit the first and second jaws 44, 46 to pass therethrough when they rotate radially outwardly. Accordingly, it is also clear from FIGS. 1 and 2 that the housing 42 serves to block rotation of the first and second jaws 44, 46 when they are entirely or partially contained within the internal passageway 43 of the housing 42. Suitable plastics for forming the housing include, but are not limited to, polytetrafluorethylene (PTFE), expanded polytetrafluoroethylene (EPTFE), polyethylene ether keytone (PEEK), polyvinylchloride (PVC), polycarbonate (PC), polyamide, polyimide, polyurethane, polyethylene (high, medium or low density), and suitable metals include stainless steel, nitinol and similar medical grade metals and alloys.

Operation of the medical device 40 will now be described with reference to FIGS. 8-12. As shown in FIG. 8, the first and second jaws 44, 46 are shown in a retracted position where they are substantially contained within the housing 42. Depending on the application, the distal ends 60, 62 of the jaws 44, 46 may slightly project from the distal end of the housing 42 in their retracted positions, or they may be entirely positioned within the housing 42. When the drive wire 22 is translated distally (to the right on the page in FIG. 8) the distal head 32 engages the driver 48, the driver 48 and jaws 44, 46 slide distally through the housing 42. The driver 48 and jaws 44, 46 slide longitudinally before they rotate (even though the rack 54 of the driver 48 is meshed with the pinions 68, 70 at the proximal ends 64, 60 of the jaws 44, 46) since the resistance to longitudinal movement is less than the force required to rotate the jaws 44, 46 (alternatively, the housing 42 can block rotation of the jaws 44, 46 when they are within the housing 42). As previously mentioned, this longitudinal movement is guided by the first and second guide surfaces 82, 84 which receive the pins 80 that slidably and pivotally connect the jaws 44, 46 to the housing 42.

Figure 10:
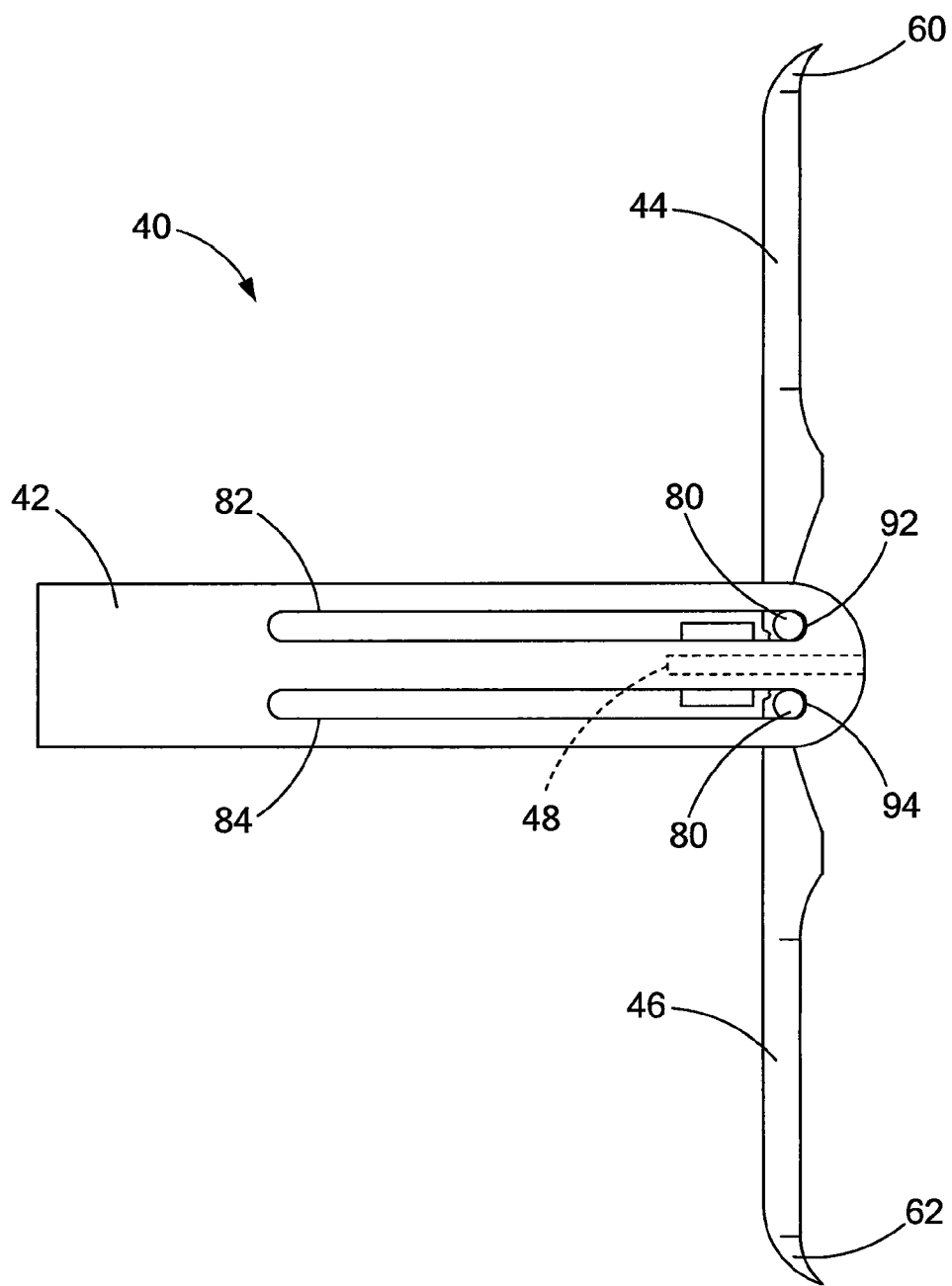

As shown in FIG. 9, the first and second jaws 44, 46 have an extended position where the jaws substantially project from a distal end of the housing 42, and their proximal ends 64, 66 are positioned adjacent the distal end of the housing 42. Accordingly, it will be seen that further distal advancement of drive wire 22, and hence the driver 48, causes the pinion 68 to rotate over the teeth 58 of the rack 54. As best seen in FIG. 10, the first and second jaws 44, 46 rotate radially outwardly from each other into a tissue receiving position. Notably, due to the presence of slots 45 at the distal end of the housing 42, the jaws 44, 46 are permitted to rotate a full 90°, thus forming at least a 180° between them. It will be recognized that through the sizing of the slots 45 and the construction of the rack 54 and pinions 68, 70, the first and second jaws 44, 46 may rotate even further away from each other.

Figure 11:
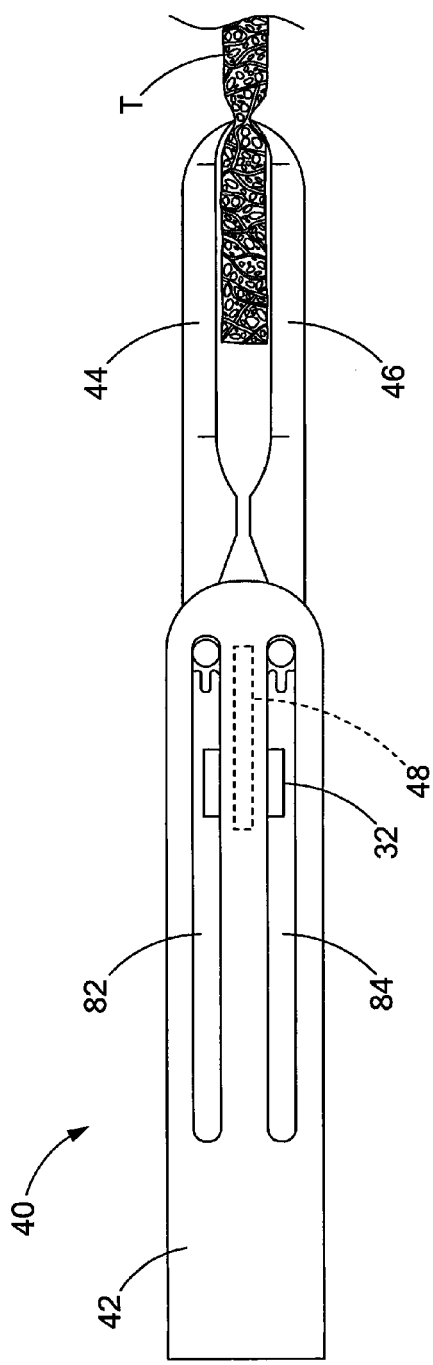
Figure 12:
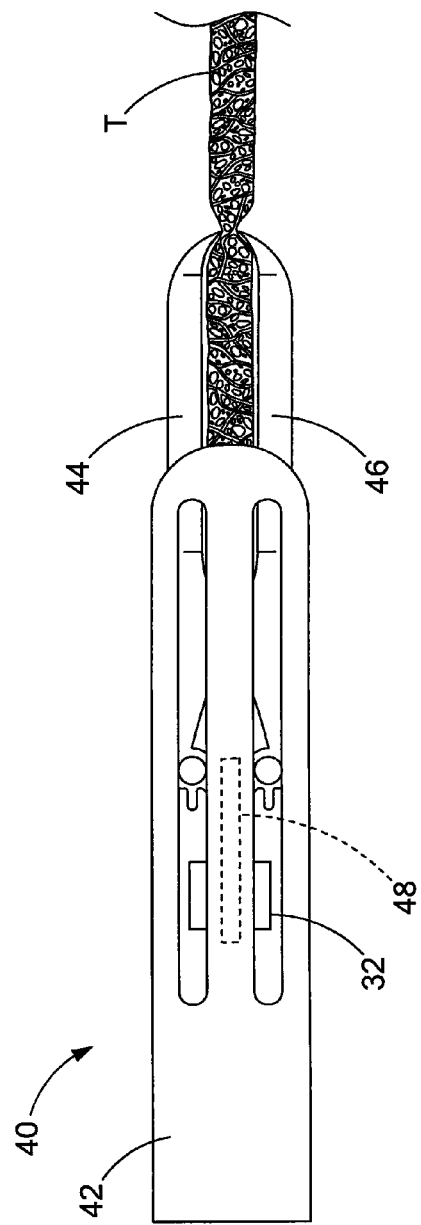

In the tissue receiving configuration shown in FIG. 10, the medical device 40 and its jaws 44, 46 may be positioned adjacent tissue T. As shown in FIG. 11, the tissue T may be placed between the first and second jaws 44, 46 and the jaws 44, 46 rotated back towards their position shown in FIG. 9. The tissue T has been shown as a single layer, although multiple layers may be clipped between the jaws 44, 46. Generally, proximal retraction of the drive wire 22 and the driver 48 again causes rotation of the first and second jaws 44, 46 to grasp the tissue T therebetween. As shown in FIG. 12, further proximal retraction of the drive wire 22 and driver 48 will cause the jaws 44, 46 to move longitudinally in a proximal direction (to the left on the page in FIG. 12).

Figure 13:
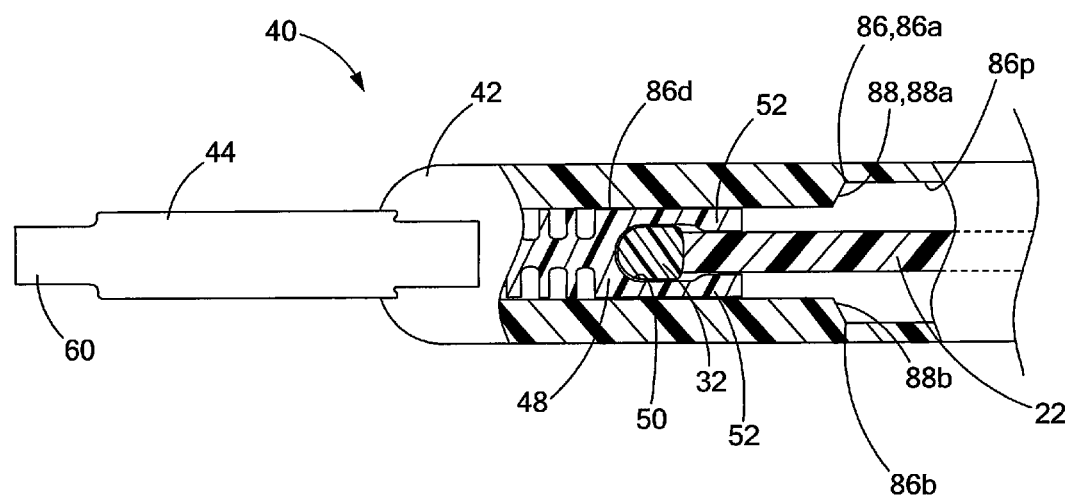
FIGS. 13 and 14 are top views, partially in cross-section, depicting operation of the medical system and device depicted in FIGS. 1-4.
Figure 14:
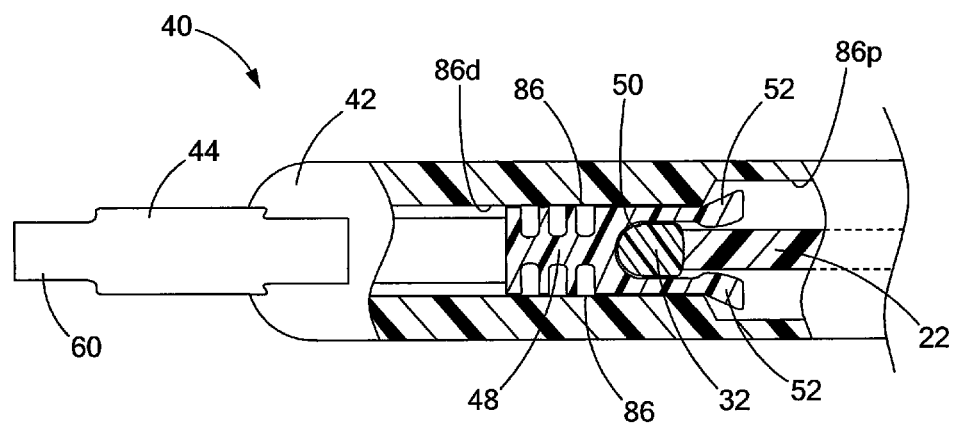

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 13, the third guide surface 86 (which guides the driver 48) includes a proximal portion 86p and a distal portion 86d. The proximal portion 86p of the third guide surface 86 has a width (measured up and down on the page in FIG. 13) that is greater than a width of the distal portion 86d of the third guide 86. As previously discussed, the third guide surface 86 is formed by opposing surfaces or C-shaped channels 86a, 86b of the housing 42. The transition between the proximal portion 86p and distal portion 86d defines a shoulder 88, and namely two shoulders 88a, 88b on opposing sides of the housing 42. The shoulders 88a, 88b are sized and positioned to engage the locking tabs 52 located on the driver 48.

As shown in FIG. 13, when the driver 48 is located within the distal portion 86d of the third guide surface 86, the locking tabs 52 are forced radially inwardly into firm frictional engagement with the drive wire 22. Stated another way, the socket 50 formed by the driver 48 to receive the distal head 32 has an entrance which is narrowed by the inward deflection of the locking tabs 52. Preferably, the locking tabs 52 plastically deform rather than elastically deform, and the tabs 52 may be bent inwardly around the distal head 32 during initial assembly of the device, and thus sized for the distal portion 86d of the third guide surface 86. In this state depicted in FIG. 13, the drive wire 22 is firmly engaged with the driver 48 and hence the first and second jaws 44, 46.

When the drive wire 22 and driver 48 are retracted proximally, for example upon grasping tissue as shown in FIG. 12, the proximal end of the driver 48 is received within the proximal portion 86p of the third guide surface 86 which has a larger width that permits radially outward movement of the locking tabs 52. Accordingly, in the state depicted in FIG. 14, the locking tabs 52 may be loosely and detachably connected to the distal head 32 of the drive wire 22. That is, the proximal retraction of the jaws 44, 46 will be limited by either the tissue T engaging the distal end of the housing 42, or the pins 80 will abut the proximal ends of the slots 82a, 82b, 84a, 84b defining a first and second guide surfaces 82, 84. As such, when proximal movement of the jaws 44, 46 and the driver 48 are thus limited, further proximal movement of the drive wire 22 and its distal head 32 may be used to withdraw the distal head 32 from the socket 50 of the driver 48. This operation may also be used to further deflect the locking tabs 52 radially outwardly. An appropriate amount of distally directed force on the drive wire 22 causes the distal head 32 to move proximally through the locking tabs 52 and plastically deform them radially outwardly. In the event the natural elasticity of the tissue T tends to pull the jaws 44, 46 out from the housing towards their extended position, the locking tabs 52, 54 will abut the shoulders 88a, 88b of the third guide surface of the housing 42 to prevent further distal movement of the jaws 44, 46.

Figure 15:
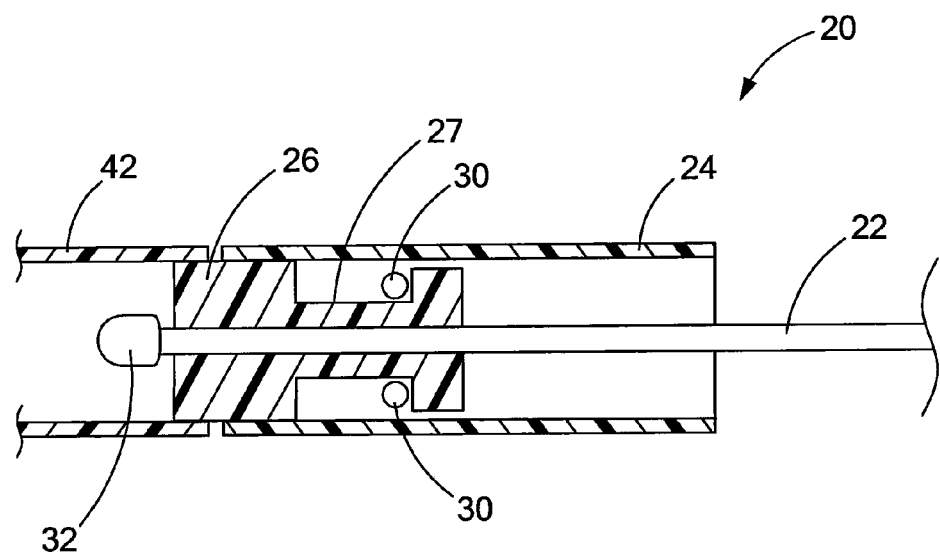
FIGS. 15 and 16 are cross-sectional views showing operation of the medical system and device depicted in FIGS. 1-4.
Figure 16:
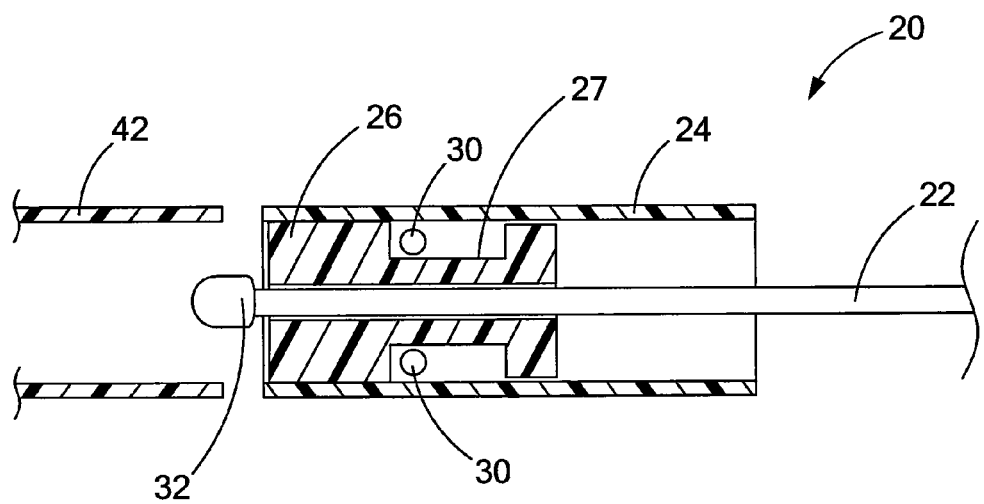

Turning now to FIGS. 15 and 16, upon still further proximal retraction of the drive wire 22 and distal head 32, the enlarged distal head 32 will abut the connection block 26 which is slidably fitted within the distal end 23 of the catheter 24. Sufficient proximal force on the drive wire 22 will overcome the frictional fit between the connection block 26 and the proximal end of the housing 42, thus moving the connection block 26 proximally (to the right on the page of FIGS. 15 and 16) to retract the connection block 26 within the tubular connector 24, as shown in FIG. 16. The catheter 24 can be used to provide a counterforce on the housing 42 while proximally retracting the drive wire 22 and connection block 26. Accordingly, the drive wire 22, catheter 24 and connection block 26 may be fully disconnected from the medical device 40, thereby leaving the first and second jaws 44, 46 and the housing 42 in a state having the tissue T clipped between the jaws 44, 46 and retained in vivo. The connection block 26 is retained at the distal end 24 of the catheter 24 via the pins 30, which are positioned within the recessed area 27 to engage the proximal and distal ends of the connection block 26 and limit its longitudinal movement.

The elongated catheter 24 (or other elongate tubular member such as a sheath, tube, scope or the like), which slidably encases the drive wire 22, extends proximally therealong to a proximal end of the system 20, and has a length suitable for placing the device 40 at any desired location within the body, while the proximal ends of drive wire 22 and catheter 24 are positioned outside of the body for use by the medical professional. Control handles (not shown) for controlling relative translation of the drive wire 22 and catheter 24 are well known in the art, and may be employed at the proximal end of the system 20.

Figure 17:
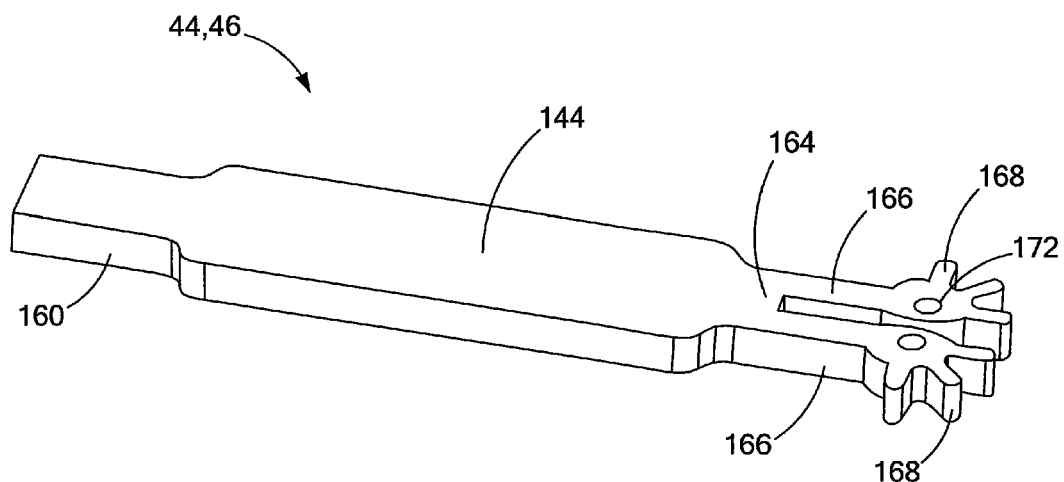
FIGS. 17 and 18 are a perspective view of an alternate embodiment of a grasping jaw forming a portion of the medical system and device of FIG. 1.
Figure 18:
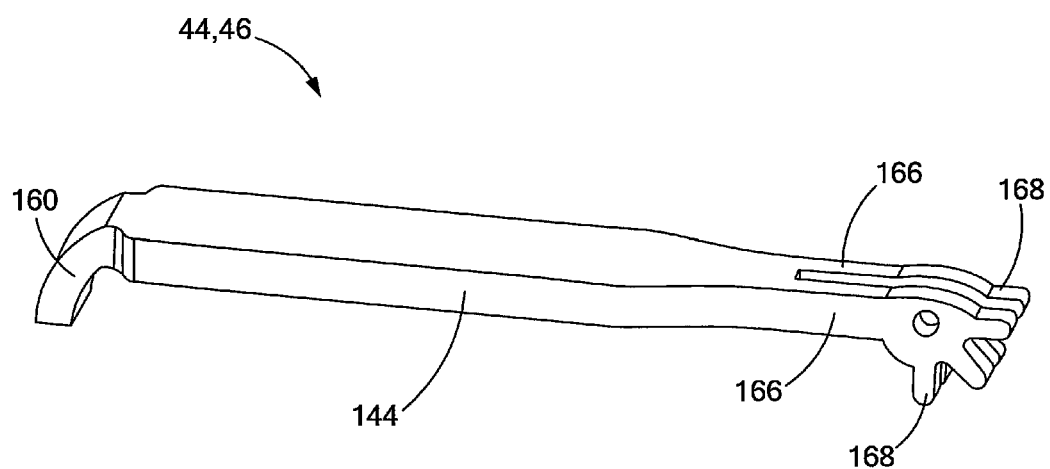

Another embodiment and method of forming the grasping jaws 44, 46 are shown in FIGS. 17-18. The jaws of the prior embodiment were generally machined, however the jaws 44, 46 may also be formed by stamping. A flat piece of metal preferably of medical grade stainless steel, is stamped into the shape 144 shown in FIG. 17. The shape includes a slightly narrow distal end 160 which then can be bent into the shape shown in FIG. 18 for grasping and engaging tissue. The distal end 160 may also be stamped to include a serrated edge, or other shapes or edge features depending upon the application. The proximal end 164 generally includes two arms 166 which lead to gears 168. As shown in FIG. 18, the gears 168 are grasped and then rotated about 90 degrees such that the gears 168 extend in a plane that is perpendicular to the plane of the sheet 144. The gears 168 also include a through-hole 172 for receiving a guiding pin. It will also be recognized that the jaws 44, 46 in this embodiment may also be formed of a single arm 166 and single gear 168.

Another embodiment of a driver 148 and drive wire 122 are shown in FIGS. 19-22. The driver 148 generally includes a socket 150 formed by two locking tabs 152. In this embodiment, a proximal portion of the locking tabs define slanted shoulders 154 which slope laterally outwardly for engagement with the third guide surface 86 in the housing 42 as previously discussed. The locking tabs 152 also include inner projections 153 which project laterally inwardly and separate the socket 150 into a distal portion 150d and a proximal portion 150p. The driver 148 again includes a central spine 156 and opposing teeth 158. In this embodiment, the distal end 166 of the driver 148 includes a pocket 168 defined by two inwardly projecting flanges 170, as will be discussed further herein. The two flanges 170 extend along a distal side of the pocket 168, and leave a gap therebetween for access to the pocket 168.

Figure 19:
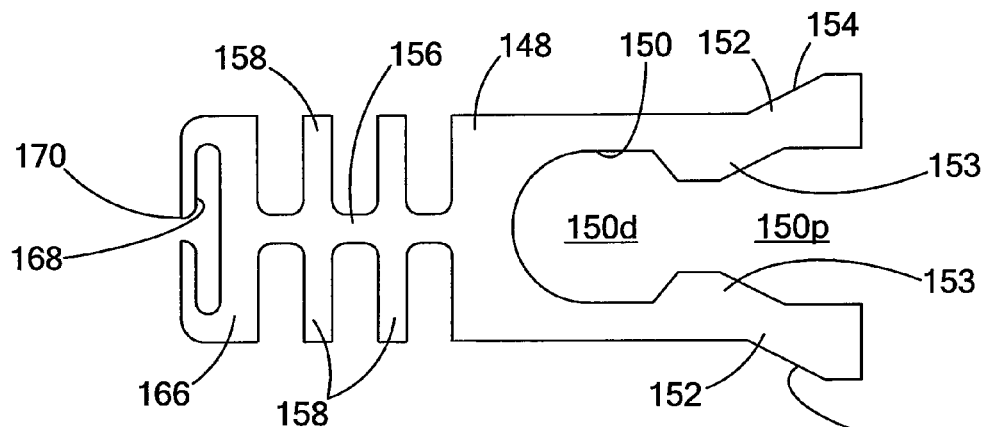
FIG. 19 is a plan view of an alternate embodiment of a driver forming a portion of the medical system and device of FIG. 1.
Figure 20:
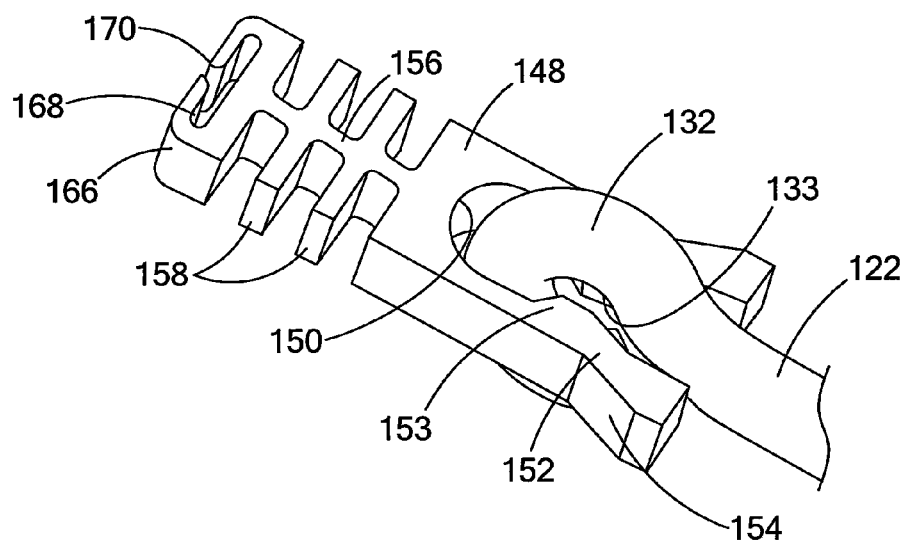
FIG. 20 is a perspective view of the driver of FIG. 19 shown attached to a drive wire.
Figure 21:
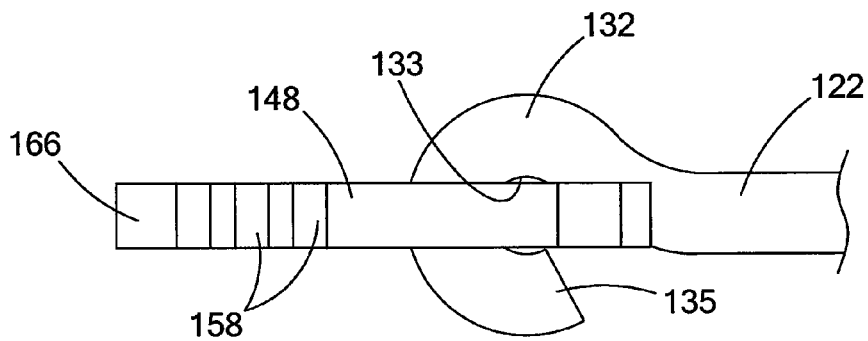
FIG. 21 is a side view of FIG. 20.

As seen in FIGS. 20 and 21, this embodiment of the drive wire 122 includes a distal head 132 which is formed by bending the distal end of the drive wire 122 into a semicircular shape as shown, preferably spanning an arc of 180 degrees to 360 degrees. Accordingly, it can be seen that the distal head 132 defines an opening 133 that is sized to receive the inner projections 153 of the locking tabs 152. As shown, the distal portion 150d of the socket 150 receives the distalmost part of the curved distal head 132, while the proximal portion of the distal head 132 projects through the proximal portion 150p of the socket 150 and proximally away therefrom. As noted above, the locking tabs 152 here are structured to be plastically deformed, and thus after formation and connection to the drive wire 122 as shown in FIG. 19, the tabs 152 are bent radially inwardly to secure the projections 153 within the opening 133 of the socket 132. In this state, the exterior shoulders 154 of the locking tabs 152 are sized to fit within the third guide surface 86, and more particularly the distal portion 86d of the third guide surface 86 without further deformation.

Figure 22A:
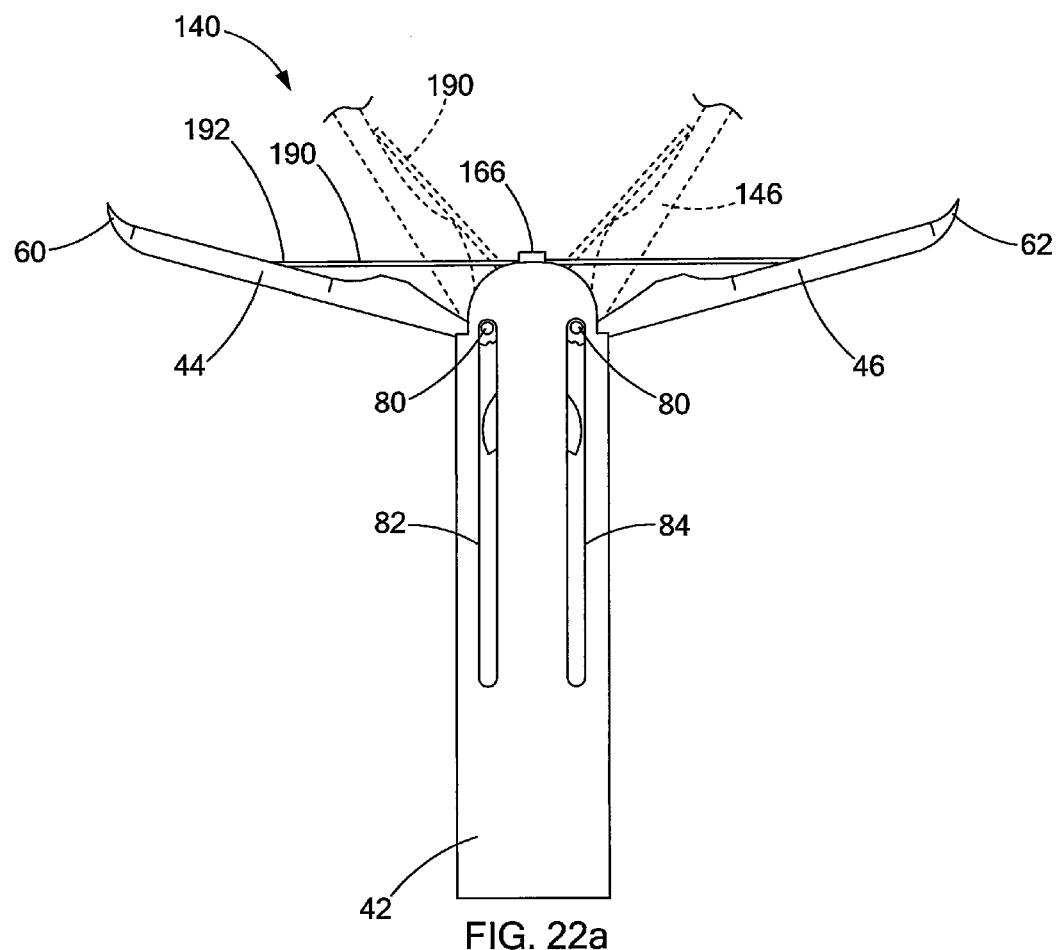
FIG. 22*a* is a plan view of an alternate embodiment of the medical device of FIG. 1.
Figure 22B:
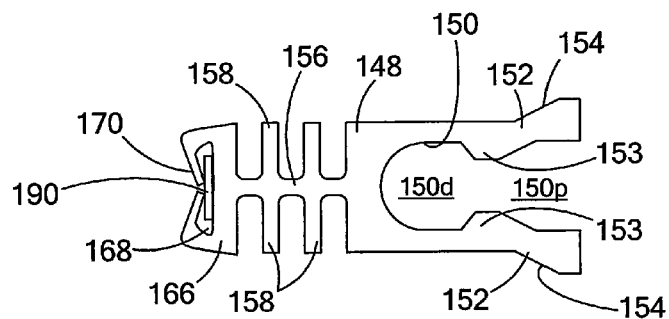
FIG. 22*b* is a plan view of the driver of FIG. 19 shown attached to a strip and forming a portion of the medical device of FIG. 22*a*.

As shown in FIGS. 22a and 22b, another embodiment of the medical device 140 may include the housing 142, grasping arms 144, 146 just as in the prior embodiment, but in this embodiment include the alternate driver 148 and an additional biasing element, namely a biasing strip 190. As best seen in FIG. 22b, the distal end 166 of the driver 148 receives the biasing strip 190 within the pocket 168. The flanges 170 are bent inwardly and proximally as shown to firmly engage the metal strip 190 and fix it to the driver 148. The biasing strip 190 is preferably a thin strip formed from a sheet of resilient material, and more preferably a metal strip, e.g. formed of stainless steel, nitinol or other super elastic alloy that is biocompatible. Accordingly, it will be recognized that as the driver 148 is moved proximally to cause the jaws 144, 146 to close, the biasing strip 190 will be forced into a V-shape or U-shape, as shown by the dotted lines in FIG. 22a.

That is, the biasing strip 190 has a straight shape in its natural, unbiased, configuration, and when bent into the V-shape it exerts a radially outward force on the jaws 144, 146. This biasing force provides the jaws 144, 146 with smooth rotation and transition between the open and closed positions. It will also be recognized that the biasing strip 190 could also have its original, unbiased position formed as a V-shape or a U-shape, and be affixed to the jaws 144, 146 such that it exerts a radially inward biasing force. The free ends 192 of the metal strip 190 simply press against the jaws 44, 46, but are not fixed or rigidly attached thereto.

Figure 23:
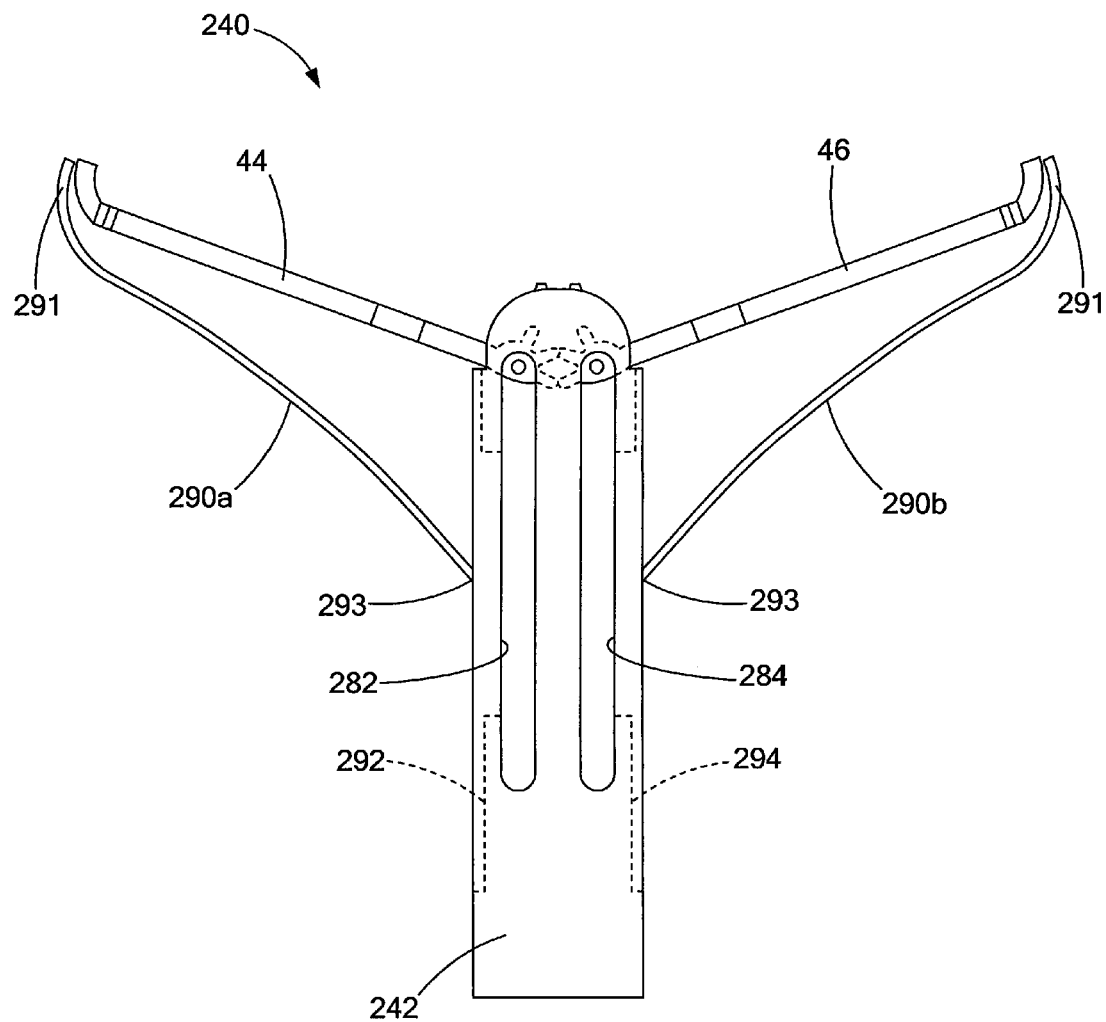
FIG. 23 is a plane view of another alternate embodiment of the medical device depicted in FIG. 1.
Figure 25:
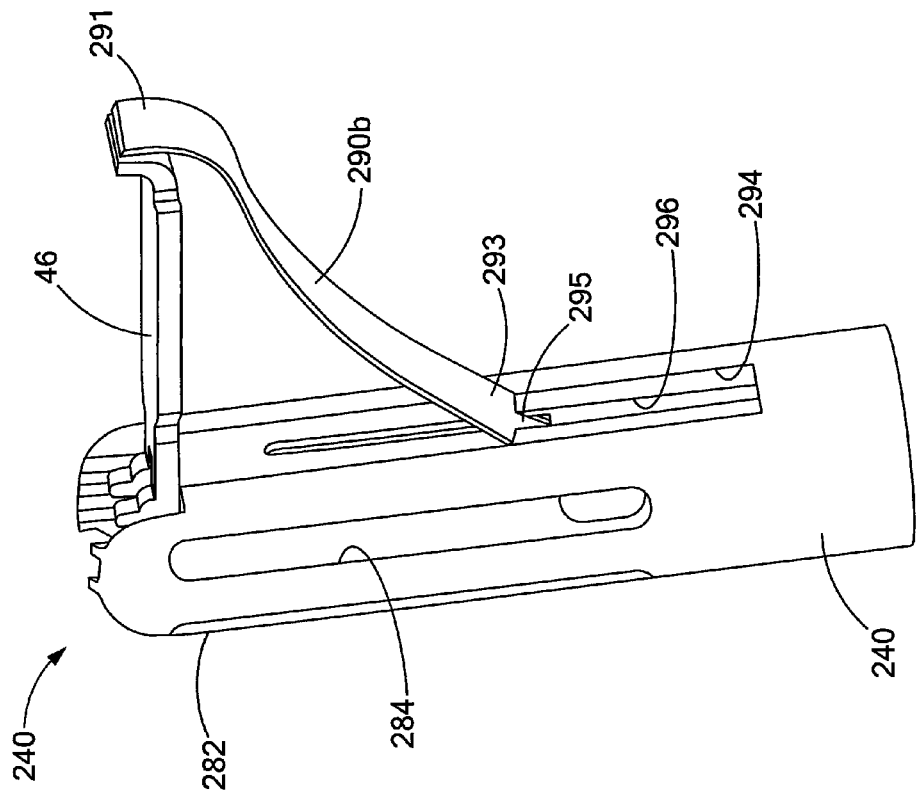
FIGS. 24 and 25 are a perspective views showing operation of the medical device depicted in FIG. 23.
Figure 24:
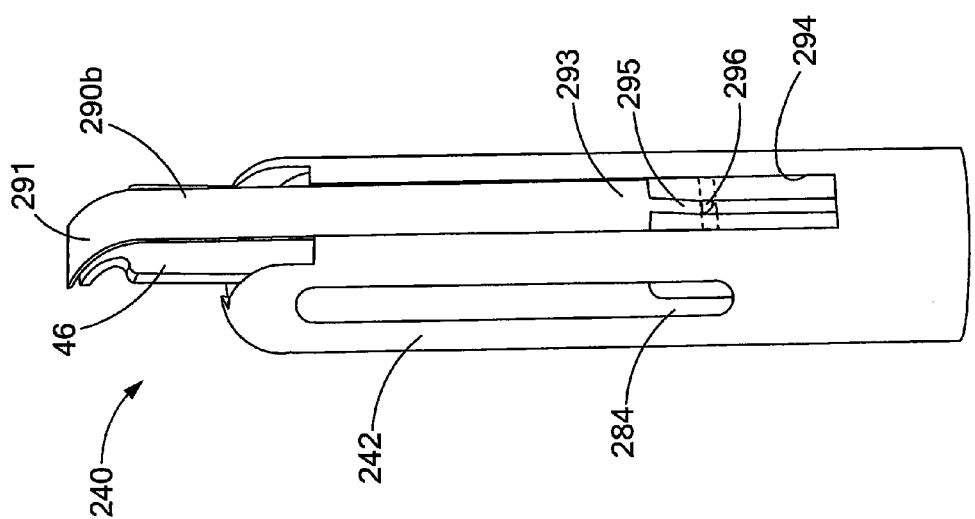

Turning to FIG. 23, another embodiment of the medical device 240 is shown, again including a housing 242 and opposing jaws 244, 246 that are slidably attached thereto. The housing 242 again includes first and second guides 282, 284 for guiding movement of the jaws 244, 246. In this embodiment however, each jaw 244, 246 includes a biasing strip 290a, 290b, respectively. The distal ends 291 of the strips 290a, 290b are fixedly attached to the exterior of the jaws 244, 246, preferably at their distal ends, and preferably by way of an adhesive, soldering, welding, or other known bonding techniques. As best seen in FIGS. 24 and 25, the housing 240 includes two exterior channels 294 on opposite sides of the housing 240 (one being shown in FIGS. 24 and 25) which are sized to receive the resilient strips 290a, 290b such that they are flush with the exterior surface of the housing in the closed/retracted configuration. The proximal ends 293 of the strips 290a, 290b include a T-shaped formed by a base 295 and cross bar 296. The base 295 extends through a smaller slot 296 formed through the housing 240. The slots 296 are coextensive with the channels 294. The cross bar 296 rides along the interior of the housing 240 and maintains the slidable connection between the strips 290 and the housing 240. Accordingly, it can be seen that the proximal ends 293 of the strips 290a, 290b are slidably and pivotably attached to the housing 240 via the channel 294 and its slot 296, allowing the strips 290a, 290b to travel with the grasping jaws 44, 46 as shown between their open and closed positions as shown in FIGS. 24 and 25.

Figure 26:
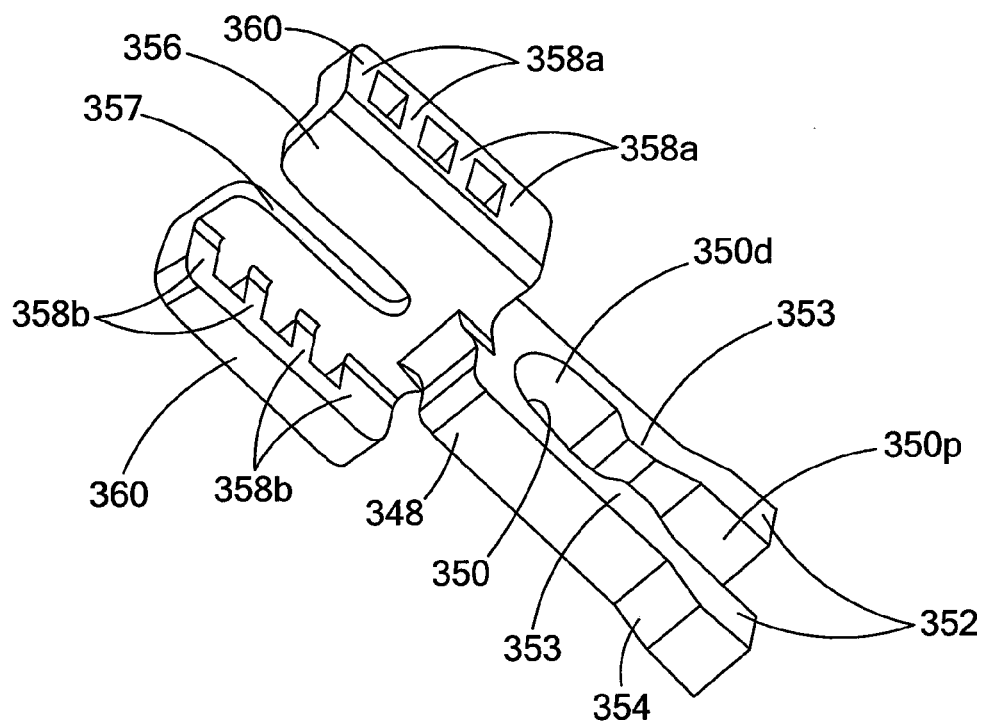
FIGS. 26 and 27 are perspective and end views, respectively, of another embodiment of a driver forming a portion of the medical system and device depicted in FIG. 1.
Figure 27:
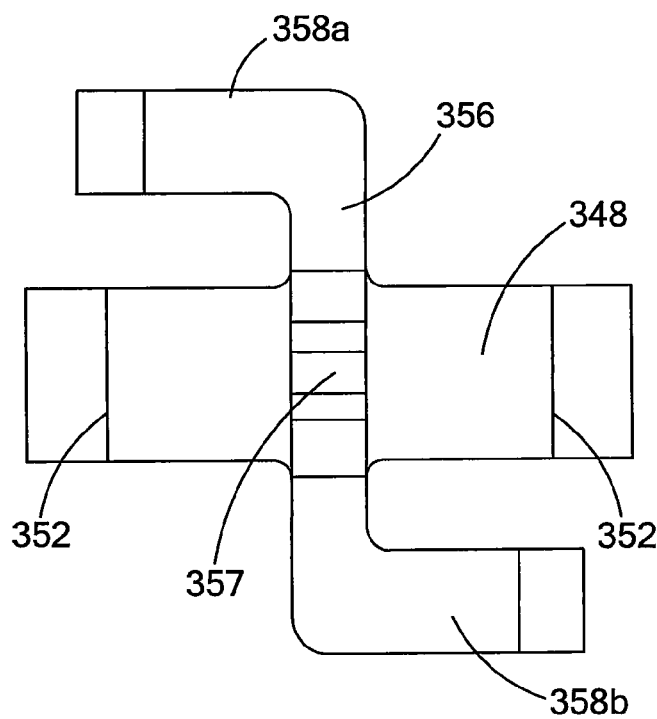
Figure 28:
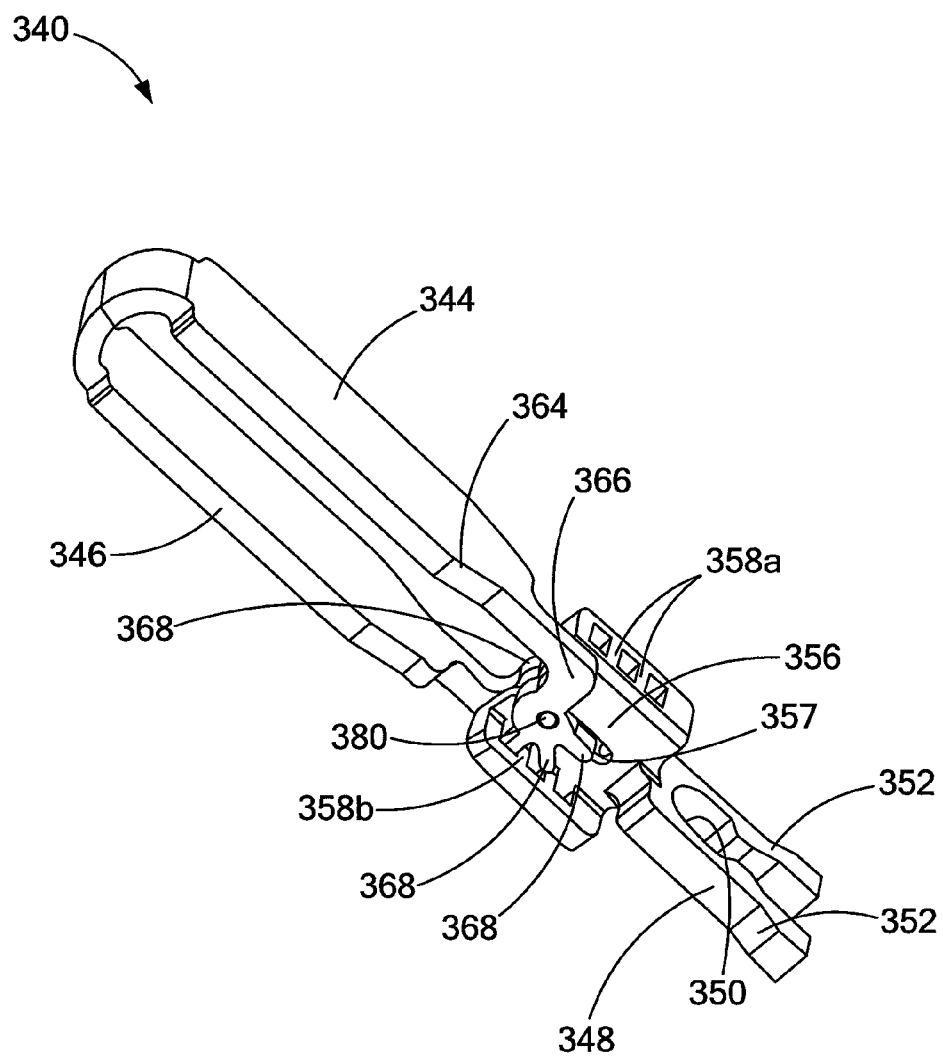
FIG. 28 is a perspective view of the driver of FIGS. 25-26 shown attached to the jaws.
Figure 29:
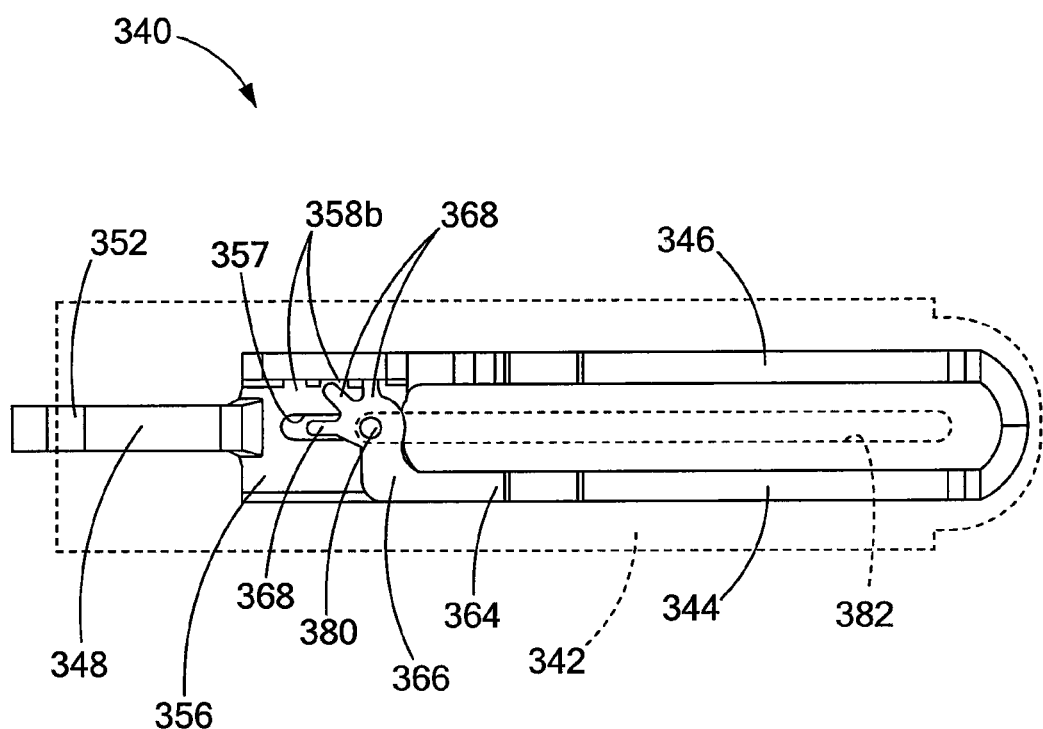
FIGS. 29 and 30 are plan views showing operation of the driver and jaws depicted in FIG. 28.
Figure 30:
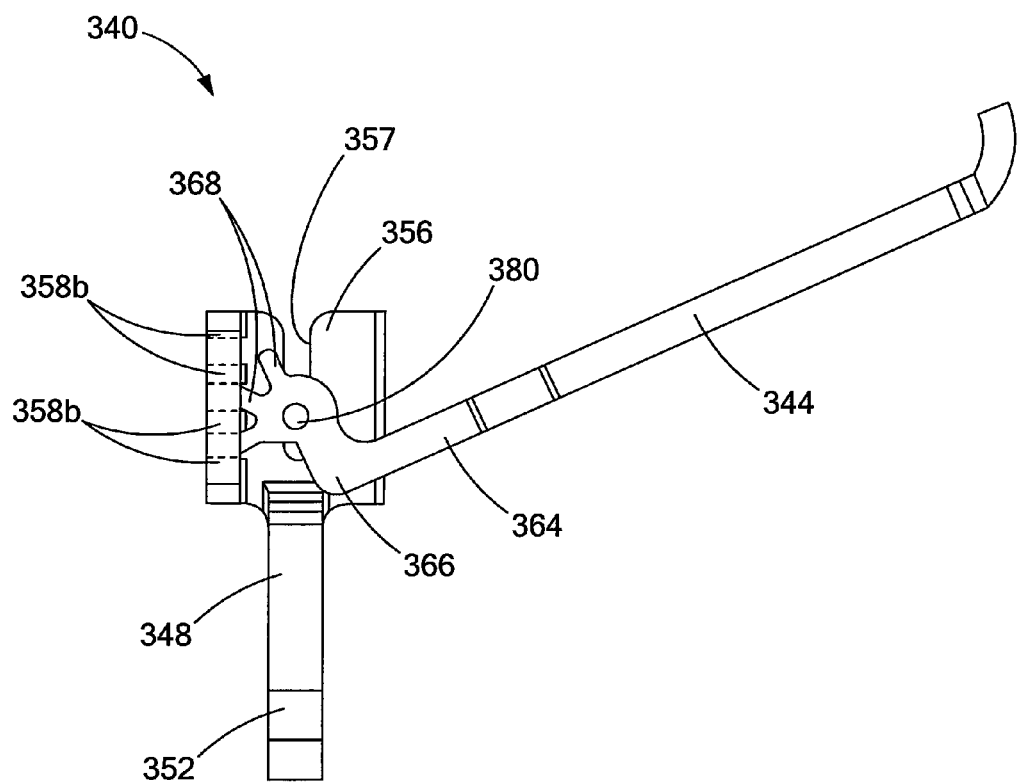

Turning now to FIGS. 26-30, another embodiment of a driver 348 is shown. As best seen in FIGS. 26 and 27, the driver 348 again includes a socket 350 formed by two locking tabs 352 which have inner projections 353 and outer shoulders 354, and which divide the socket 350 into a distal portion 353 and a proximal portion 350p. Unlike the prior embodiments of the driver, in this embodiment the distal portion defines a geared rack that has a Z-shape. Generally, a central plate 356 replaces the central spine 56, 156 of the prior embodiments, and the plate 356 extends in a plane that is parallel to the longitudinal plane of the housing 342 (FIG. 29). The plane of the central plate 356 is also perpendicular to a plane of the proximal half of the driver 348 (i.e. that which includes the socket 350 and tabs 352). A first set of teeth 358a project laterally away from the central plate 356 in a first direction, while a second set of teeth 358b project laterally away from the central plate 356 in a second direction. The first and second sets of teach 358a, 358b extend from opposite ends of the central plate 356, and the first and second directions are generally opposite each other. The sets of teeth 358a, 358b are each securely held to the central plate 356 by two outer frames 360 which extend around the periphery of the teeth 358a, 358b.

Accordingly, and as best seen in FIG. 28, the medical device 340 includes first and second grasping jaws 344, 346 each having a proximal end 366 and gear teeth 368 which have been bent to project orthogonally away from a main body of the jaw 344. Accordingly, the first set of teeth 358a receive the gear 368 of the second jaw 346, while the second set of teeth 358b receive the gear 368 of the first jaw 344. Notably, having the proximal ends 366 of the jaws 344, 346 bent laterally/orthogonally as shown allows a single pin 380 to be passed through the gears 368 and thus shared by both jaws 344, 346. Still further, and as shown in FIG. 29, the housing 342 may thus include only a single guide surface 382 formed by a single slot on each lateral side of the housing 342 for receiving the ends of the single pin 380. It can be seen that the first and second jaws 344, 346 thereby share a single guide surface 382 (a jaw guide surface) and guide slot, thus ensuring their coordinated operation and smooth opening and closing.

As also shown in FIG. 29, a slot 357 is formed in the central plate 356, and is aligned with the pin 380 and jaw guide surface 382 to receive the pin 380 as the driver 348 moves forwardly relative to the jaws 344, 346. As discussed above and shown in FIG. 30, when the pin 380 (shared by proximal ends 366 and gears 368 of the jaws 344, 346) has hit the distal end of the single jaw guide surface 382, the driver 348 will continue moving distally to cause the gears 368 to rotate via the rack/teeth 358a, 358b of the driver 348, thereby inducing rotation of the jaws 344, 346.

Figure 33:
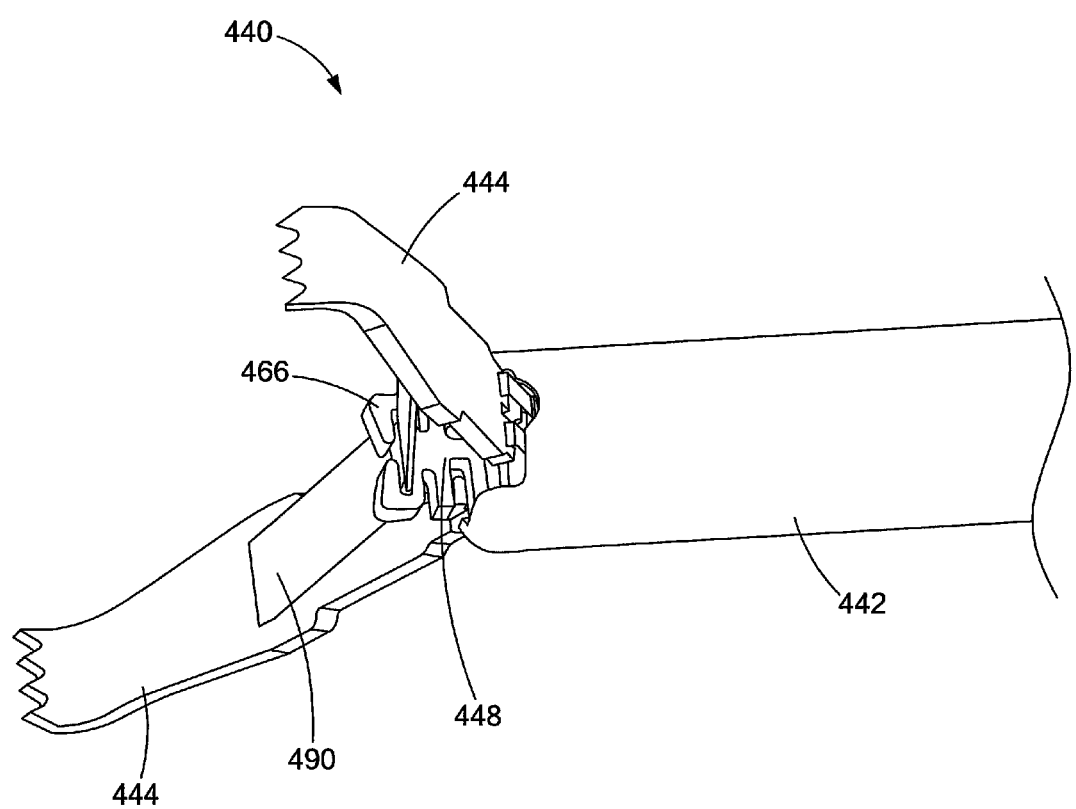
FIG. 33 is a perspective view of the medical system and device depicted in FIGS. 31 and 32.

Turning to FIGS. 31-33, another embodiment of the medical system 420 and medical device 440 are depicted. In this embodiment, medical system 420 again includes a drive wire 422 having a distal head 432 which is formed by bending the distal end of the drive wire 422 into the shape shown. The medical system 420 also includes a catheter attachment 430 which is generally a tubular member that is connected to the distal end of the catheter 24 and is used to slidably receive the connection block 426. The catheter attachment 430 includes a pair of openings 434 to provide access to the control wire 422 and the connection block 426, whereby a tool may be used to hold the connection block 426 in either a retracted or extended position, as further described in copending U.S. Appln. Nos. 61/391,878 and 61/391,875, the disclosures of which are hereby incorporated by reference in their entirety.

The medical device 440 includes a housing 442 which is detachably connected to the catheter 24 and its catheter attachment 430 via the connection block 426. The housing 442 slidably receives the pair of jaws 444 which are connected to the drive wire 422 via the driver 448. As with the previous embodiments, the driver 448 includes a socket 450 defined by locking tabs 452 which releasably engage the distal head 432 of the drive wire 422. The distal portion of the driver 448 includes a plurality of teeth 458 which define a gear or rack which serves to drive rotation of the jaws 444 as previously described. The distal end 466 of the driver 448 includes a pocket defined by flanges which are used to fixably engage the biasing strip 490. The housing 442 further defines a pair of guiding surfaces or slots 482 which guide the longitudinal and rotational movement of the jaws 444.

In this embodiment, the jaws 444 and housing 442 are structured such that in the fully retracted position (shown), the jaws 44 project (at least partially) out distally from the end of the housing 442. As best seen in FIG. 32, as the distal head 432 is pushed through the locking tabs 452 they are plastically deformed outwardly to engage the shoulders 446 in the housing, and the jaws 444 are fully retracted. In this way, the length of the housing 442 can be shortened, as can the guiding slots 482 therein for guiding the jaws 444. It can also be seen in FIG. 32 that the distal ends of the jaws 444 include serrations 445 or other structures which may aid in gripping tissue.

It is also noted that in this embodiment, as with all prior embodiments, the drive wire 422 is capable of transmitting rotational force and torque (e.g. from the proximal operating end of the system 20/420) through the distal head 432 and the driver 448 to the jaws 444. As such the medical device 440 may be rotated via rotation of the drive wire 422, i.e. the jaws 444, jaw pins (e.g. 80), housing 442, and driver 448 all rotate as a unit relative to the catheter 24. Inasmuch as the housing 442 may also be non-rotatably connected to the connection block 426 (e.g. depending on the friction therebetween), the connection block 426 may also rotate within the catheter attachment 430 (or the catheter, e.g. 24) when the catheter attachment 430 is not used. Accordingly, the orientation of the jaws 444 may be rotated through rotation of the proximal end of the drive wire 422 to orient the jaws relative to the tissue or material being grasped or clipped. It has been found that forming the drive wire 422 out of a solid nitinol wire has provided good torque transmission for rotation of the medical device 440.

It has also been found that having the jaws 444 project at least partially out of the housing 442 in their fully retracted position allows the orientation of the jaws 444 to be visualized so that it is easier to rotate the jaws 444 prior to opening and closing them around tissue. Still further, additional tissue may be encapsulated in the jaws 444 before the tissue abuts the distal end of the housing 442. The distance which the jaws 444 project from the housing 442 may be varied depending upon a particular application, i.e. sized to correspond to the thickness of the tissue or the type of procedure being formed to insure good spacing between the distal ends of the jaws 444 and the distal end of the housing 442.

Figure 37:
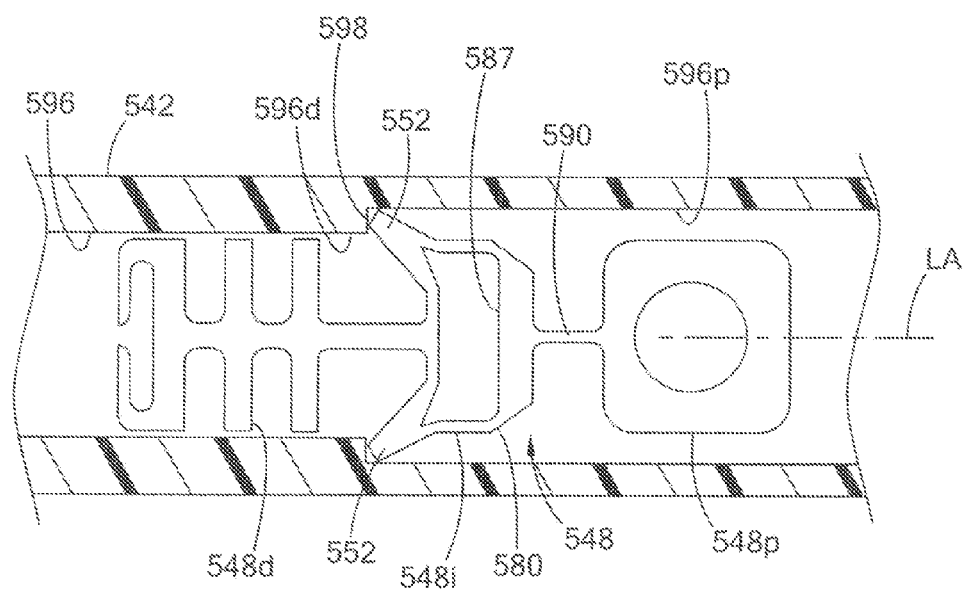
Figure 38:
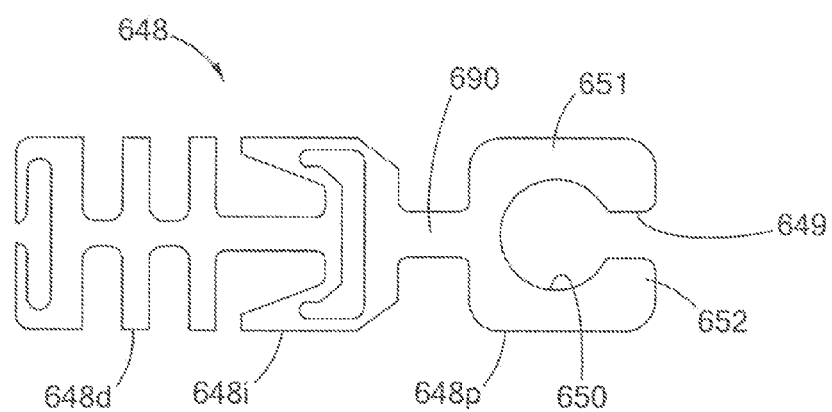
FIG. 38 is a plan view of yet another alternate embodiment of a driver forming a portion of the medical system and device of FIG. 1.

Yet another embodiment of a driver 548 is shown in FIGS. 34-37, and a variation thereof in FIG. 38. The driver 548 again generally includes a proximal portion 548p, a distal portion 548d, and an intermediate portion 548i therebetween. The proximal portion 548p again defines a socket 550, here formed by a solid frame or ring 551. The drive wire thus preferably includes a distal head such as the hook 132 (FIGS. 20-21) or other shape than can fit through the socket 550 and longitudinally engage the driver 548. As with some of the prior embodiments, the distal portion 548d of the driver 548 again includes a central spine 556 and opposing teeth 558 to form a rack that rotates the grasping jaws. The distal end 566 of the driver 548 includes a pocket 568 defined by two inwardly projecting flanges 570 to engage an optional biasing strip, as discussed above.

Figure 34:
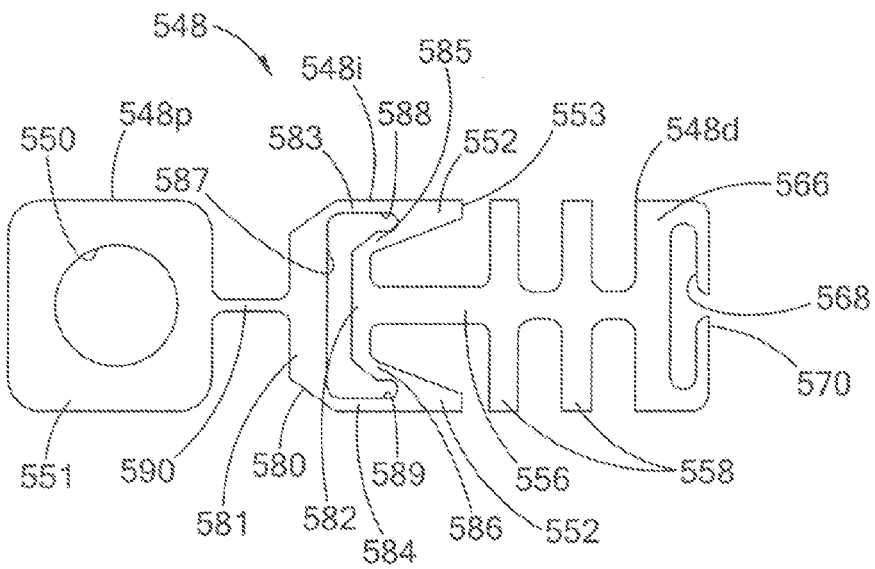
FIGS. 34-37 are plan views showing operation of another alternate embodiment of a driver forming a portion of the medical system and device of FIG. 1.
Figure 35:
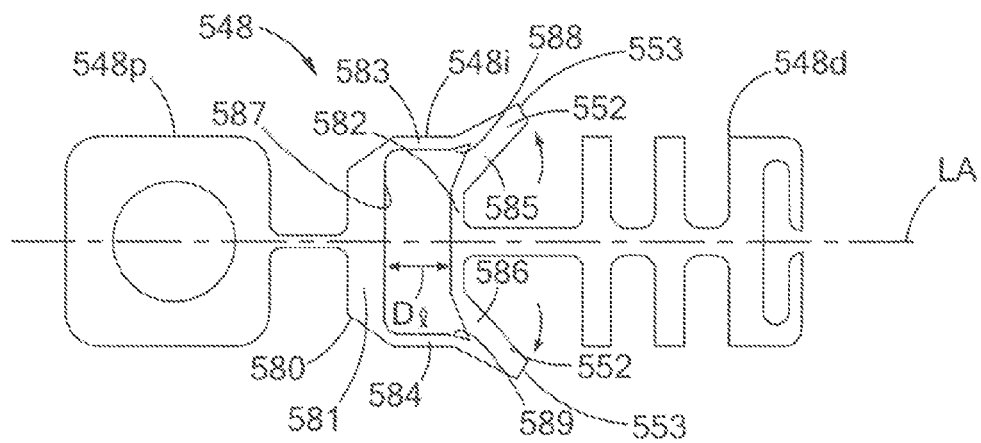
Figure 36:
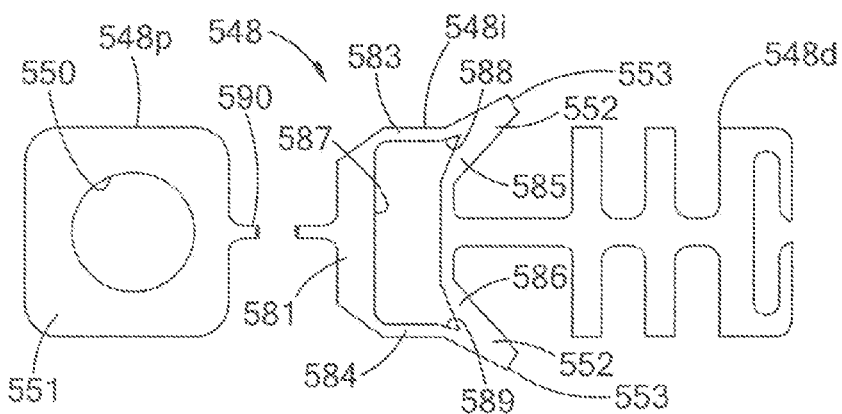

In this embodiment, the intermediate portion 548i of the driver 548 is structured to be deformable, whereby locking legs 552 move laterally/radially outwardly to engage the housing 543 (FIG. 37) and lock the jaws to prevent them from sliding distally and rotating open. As best seen in FIGS. 34 and 35, the intermediate portion 548i includes a deformable frame 580 including a proximal member 581, a distal member 582, and two opposing lateral members 583, 584, which together define an enclosed intermediate space 587 therebetween. The proximal member 581 is connected to the driver's proximal portion 548p via a thin neck 590 directly connected to the ring 551 of socket 550, discussed further herein. The distal member 582 is connected to the driver's distal portion 548d via the central spin 556 as shown. The distal member 582 further includes deformable areas 585, 586 at its lateral ends, which are structured to deform and thus serve as living hinges. Preferably the frame 580 plastically deforms to permanently lock the clip.

The locking legs 552 are formed in the intermediate portion 548i at the locations where the lateral members 583, 584 meet the distal member 582, and in particular the deformable areas 585, 586. The locking legs 552, alone or in combination with the lateral and distal members 582, 583, 584, define extensions 588, 589 of the intermediate space 587, and generally have a V-shape or U-shape. Stated another way, the intermediate space 587 has a general C-shape in the normal operating condition shown in FIG. 34.

Upon application of a predetermined force differential between the driver's proximal portion 548p and distal portion 548d, the frame 580 deforms such that the locking legs move outwardly away from the longitudinal axis LA, as shown by the arrows in FIG. 35. In particular, the longitudinal distance (denoted by $D_l$ in FIG. 35) of the intermediate space increases (as does the overall length of the driver 548), and the intermediate space changes from its general C-shape to a generally rectangular shape. As best seen in FIG. 35, the deformation of the frame 580 primarily occurs within the deformable areas 585, 586 of the distal member 582, however the lateral members 583, 584 and/or the locking legs 552 may also slightly deform when the driver 548 is stretched due to the force differential. The force differential is generally caused by the user placing a proximally directed force of the drive wire while the grasping jaws are engaged with tissue (or other material) and engaged with the distal end of the housing such that further proximal withdrawal of the jaws is blocked.

Upon deformation of the frame 580 and rotation of the locking legs 552 outwardly, further proximal force on the drive wire will induce a second force differential between the driver's proximal portion 548p and the intermediate portion 548i, whereupon the neck 590 is designed to fail such that the drive wire (still attached to proximal portion 548 via socket 550) can be moved further proximally to detach the delivery catheter from the housing of the clip, leaving the clip in place and locked on the tissue. FIG. 37 shows an alternate housing 532, which includes a driver guide surface 596. A proximal section 596p of the guide surface 596 is wider than the distal section 596d, thereby forming a shoulder 598 that can be engaged by the contact surfaces 553 of the locking legs 552. The contact surfaces 553 have been shown as frusto-conical in shape, but may be pointed or rectangular. Similarly, the shoulder 598 is shaped to be engaged by the legs 552, and is orthogonal to the longitudinal axis LA, and may even be sloped proximally (i.e. to the right on the page in FIG. 37). Multiple shoulders 598 may also be formed to create a one-way ratcheting mechanism.

A variation of the driver 548 described above is shown in FIG. 38. This driver 648 includes a distal portion 648d and an intermediate portion 648i similar to those described above. In this variation, the neck 690 is not designed to fail under a predetermined load (force differential), but rather the proximal portion 648p of the driver 648 is designed to release the drive wire under a predetermined force. Here the outer ring 651 defining the socket 650 includes a throat 649 that is deflectable and provides the socket 650 with a proximally facing opening. At the same time, the proximal portion 648p does not include the locking tabs, but rather the intermediate portion 648i again defines locking legs 652 which operate as described above with reference to legs 552.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for engaging tissue, the medical device comprising:
    a housing defining an internal passageway and a longitudinal axis extending between proximal and distal ends of the housing, the housing defining a driver guide surface along the internal passageway;
    a first jaw rotatable relative to the housing, the first jaw having proximal and distal ends;
    a second jaw rotatable relative to the housing, the second jaw having proximal and distal ends;
an elongated drive wire; and
    a driver having a proximal portion engaged with the drive wire and a distal portion engaged with the proximal ends of the first and second jaws, longitudinal movement of the driver rotating the first and second jaws relative to the housing, the driver including an intermediate portion positioned between the proximal and distal portions, the intermediate portion including a frame and a locking leg connected to the frame, the frame defining an intermediate space, the frame being deformable such that a predetermined longitudinal force differential between the proximal portion and distal portion of the driver causes the frame to deform and the locking leg to move away from the longitudinal axis into a locking position for engaging the driver guide surface.

2. The medical device of claim 1, wherein a length of the driver increases upon deformation of the frame.

3. The medical device of claim 1, wherein the frame circumscribes the intermediate space.

4. The medical device of claim 1, wherein the intermediate space has a general C-shape prior to deformation of the frame, and a generally rectangular shape after deformation of the frame.

5. The medical device of claim 1, wherein a longitudinal distance of the intermediate space increases after deformation.

6. The medical device of claim 1, wherein the locking leg rotates away from the longitudinal axis.

7. The medical device of claim 1, wherein the frame plastically deforms.

8. The medical device of claim 1, wherein the frame includes a proximal member extending laterally, a distal member extending laterally, and a pair of side members connecting the proximal and distal members.

9. The medical device of claim 8, wherein the locking leg is connected to the distal member and one of the side members.

10. The medical device of claim 9, wherein the distal member defines a deformable area adjacent the locking leg.

11. The medical device of claim 9, wherein the distal member, locking leg, and the one side member together deform under the predetermined longitudinal force differential to move the locking leg away from the longitudinal axis.

12. The medical device of claim 9, further comprising a second locking leg connected to the distal member and one of the side members.

13. The medical device of claim 1, wherein the locking leg has a general V-shape and defines a portion of the intermediate space.

14. The medical device of claim 1, further comprising a neck interconnecting the proximal portion of the driver and the intermediate portion of the driver.

15. The medical device of claim 14, wherein the neck is breakable upon a second predetermined longitudinal force differential between the proximal portion and the intermediate portion of the driver.

16. The medical device of claim 15, wherein the second predetermined longitudinal force differential is greater than the predetermined longitudinal force differential that deforms the frame.

17. The medical device of claim 1, wherein the first jaw has a proximal end slidably and pivotally connected to the housing, the first jaw slidably received within the internal passageway for longitudinal movement between an extended position and a retracted position, and wherein the second jaw has a proximal end slidably and pivotally connected to the housing, the second jaw slidably received within the internal passageway for longitudinal movement between an extended position and a retracted position.

18. The medical device of claim 17, wherein the proximal ends of the first and second jaws include gears having teeth, and wherein the driver includes corresponding teeth that mesh with the teeth of the jaws.

19. The medical device of claim 17, wherein the proximal ends of the first and second jaws are formed as pinions, and wherein the driver is formed as a rack, wherein longitudinal movement of the driver and rack rotates the pinions of the first and second jaws in their extended positions.

20. The medical device of claim 1, wherein the driver is formed as a unitary single piece.

21. The medical device of claim 1, wherein the force of differential comprises a proximal force on the proximal portion relative to the distal portion of the driver.

22. A medical device for engaging tissue, the medical device comprising:
    a housing defining an internal passageway and a longitudinal axis extending between proximal and distal ends of the housing, the housing defining a driver guide surface along the internal passageway;
    a first jaw rotatable relative to the housing, the first jaw having proximal and distal ends;
    a second jaw rotatable relative to the housing, the second jaw having proximal and distal ends;
an elongated drive wire; and
    a driver having a proximal portion engaged with the drive wire and a distal portion engaged with the proximal ends of the first and second jaws, longitudinal movement of the driver rotating the first and second jaws relative to the housing, the driver including an intermediate portion positioned between the proximal and distal portions, the intermediate portion including a frame and a locking leg connected to the frame, the frame defining an intermediate space, the frame being deformable such that a predetermined longitudinal force differential between the proximal portion and distal portion of the driver causes the frame to deform and the locking leg to move away from the longitudinal axis into a locking position for engaging the driver guide surface;
wherein the driver guide surface includes a proximal portion and distal portion and a shoulder between the proximal and distal portions, the shoulder facing proximally, and wherein the locking leg is positioned to engage the shoulder to limit longitudinal movement of the driver after the locking leg has been moved laterally outwardly by deformation of the frame of the driver.

* * * * *